(12) United States Patent
Nygaard et al.

(10) Patent No.: US 9,575,013 B2
(45) Date of Patent: Feb. 21, 2017

(54) NON-CONTACT METHOD AND SYSTEM FOR INSPECTING A MANUFACTURED PART AT AN INSPECTION STATION HAVING A MEASUREMENT AXIS

(71) Applicant: GII ACQUISITION, LLC, Davisburg, MI (US)

(72) Inventors: Michael G. Nygaard, Fenton, MI (US); Nathan Andrew-Paul Kujacznski, Flint, MI (US)

(73) Assignee: GII ACQUISITION, LLC, Davisburg, MI (US)

( * ) Notice: Subject to any disclaimer, the term of this patent is extended or adjusted under 35 U.S.C. 154(b) by 0 days.

(21) Appl. No.: 14/629,527

(22) Filed: Feb. 24, 2015

(65) Prior Publication Data

US 2015/0204798 A1 Jul. 23, 2015

Related U.S. Application Data

(63) Continuation-in-part of application No. 14/050,907, filed on Oct. 10, 2013, now Pat. No. 9,019,489, which
(Continued)

(51) Int. Cl.
*G01N 21/95* (2006.01)
*G01B 11/24* (2006.01)
(Continued)

(52) U.S. Cl.
CPC ............ *G01N 21/952* (2013.01); *B07C 5/342* (2013.01); *F42B 35/00* (2013.01);
(Continued)

(58) Field of Classification Search
USPC .... 356/237.1–241.6, 242.1–243.8, 426–431, 356/600–640
See application file for complete search history.

(56) References Cited

U.S. PATENT DOCUMENTS 3,411,009 A 11/1968 Ford et al.
3,604,940 A 9/1971 Matthews
(Continued)

FOREIGN PATENT DOCUMENTS

EP 0047936 A1 3/1982
JP 2008073653 A 4/2008
(Continued)

OTHER PUBLICATIONS

International Preliminary Report on Patentability; related International application No. PCT/US2014/016390; date of issuance of report Nov. 3, 2015.
(Continued)

*Primary Examiner* — Tri Ton
*Assistant Examiner* — Jarreas C Underwood
(74) *Attorney, Agent, or Firm* — Brooks Kushman P.C.

(57) ABSTRACT

A method and system for inspecting a manufactured part at an inspection station are provided. A supported part is rotated about a measurement axis so that the part moves at predetermined angular increments during at least one rotational scan. A backside beam of collimated radiation is directed at and is occluded by the supported part at each of a first plurality of consecutive increments of movement to create a stream of unobstructed portions of the backside beam in rapid succession passing by and not blocked by the supported part. A frontside beam of radiation is directed at and is reflected by the supported part at each of a second plurality of consecutive increments of movement to create a stream of reflected portions of the frontside beam in rapid succession. The streams of reflected and unobstructed portions are detected at the inspection station to obtain electrical signals which are processed.

19 Claims, 12 Drawing Sheets

Related U.S. Application Data is a continuation of application No. 13/109,369, filed on May 17, 2011, now Pat. No. 8,570,504, application No. 14/629,527, which is a continuation-in-part of application No. 13/414,081, filed on Mar. 7, 2012.

(51) Int. Cl.
| | | |
|---|---|---|
| *G01N 21/952* | (2006.01) | |
| *B07C 5/342* | (2006.01) | |
| *F42B 35/00* | (2006.01) | |
| *G01N 21/90* | (2006.01) | |

(52) U.S. Cl.
CPC ....... *G01B 11/2433* (2013.01); *G01N 21/909* (2013.01); *G01N 21/9515* (2013.01); *G01N 2201/02* (2013.01); *G01N 2201/0621* (2013.01); *G01N 2201/0638* (2013.01); *G01N 2201/12* (2013.01)

(56) References Cited

U.S. PATENT DOCUMENTS

| | | | |
|---|---|---|---|
| 3,924,953 A | 12/1975 | Allard | |
| 4,280,624 A * | 7/1981 | Ford | B07C 5/126 209/524 |
| 4,315,688 A | 2/1982 | Pryor | |
| 4,547,674 A | 10/1985 | Pryor et al. | |
| 4,598,998 A | 7/1986 | Kamei et al. | |
| 4,636,635 A * | 1/1987 | Kronseder | G01N 21/9009 209/526 |
| 4,644,394 A * | 2/1987 | Reeves | G01N 21/952 33/199 B |
| 4,691,231 A * | 9/1987 | Fitzmorris | B07C 5/3408 209/522 |
| 4,721,388 A | 1/1988 | Takagi et al. | |
| 4,831,251 A | 5/1989 | Hanna | |
| 4,852,983 A | 8/1989 | Fein | |
| 4,906,098 A | 3/1990 | Thomas et al. | |
| 4,912,318 A * | 3/1990 | Kajiura | B07C 5/126 209/526 |
| 4,923,066 A * | 5/1990 | Ophir | F42B 35/00 209/538 |
| 4,969,746 A * | 11/1990 | McConnell | A24C 5/3412 209/577 |
| 4,970,401 A | 11/1990 | Sadeh et al. | |
| 4,983,043 A | 1/1991 | Harding | |
| 5,012,117 A | 4/1991 | Karafa et al. | |
| 5,024,529 A | 6/1991 | Svetkoff et al. | |
| 5,098,031 A | 3/1992 | Hitomi | |
| 5,164,995 A | 11/1992 | Brooks et al. | |
| 5,168,458 A | 12/1992 | Gomes | |
| 5,170,306 A | 12/1992 | Gomes | |
| 5,291,272 A | 3/1994 | Demirsu | |
| 5,383,021 A | 1/1995 | Hanna | |
| 5,521,707 A | 5/1996 | Castore et al. | |
| 5,546,189 A | 8/1996 | Svetkoff et al. | |
| 5,568,263 A | 10/1996 | Hanna | |
| 5,608,530 A | 3/1997 | Gates | |
| 5,617,209 A | 4/1997 | Svetkoff et al. | |
| 5,646,724 A | 7/1997 | Hershline | |
| 5,815,275 A | 9/1998 | Svetkoff et al. | |
| 5,975,710 A | 11/1999 | Luster | |
| 6,038,521 A | 3/2000 | Kanai | |
| 6,055,329 A | 4/2000 | Mufti | |
| 6,098,031 A | 8/2000 | Svetkoff et al. | |
| 6,122,045 A | 9/2000 | Pike et al. | |
| 6,252,661 B1 | 6/2001 | Hanna | |
| 6,285,034 B1 * | 9/2001 | Hanna | G01B 11/245 250/559.2 |
| 6,289,600 B1 | 9/2001 | Watts | |
| 6,313,948 B1 | 11/2001 | Hanna | |
| 6,324,016 B1 | 11/2001 | Luster | |
| 6,959,108 B1 | 10/2005 | Bartelt et al. | |
| 7,065,242 B2 | 6/2006 | Petrov et al. | |
| 7,312,607 B2 | 12/2007 | Nygaard | |
| 7,329,855 B2 * | 2/2008 | Katayama | G01N 21/9054 250/223 B |
| 7,403,872 B1 | 7/2008 | St. Onge et al. | |
| 7,633,046 B2 | 12/2009 | Spalding | |
| 7,633,634 B2 | 12/2009 | Spalding et al. | |
| 7,633,635 B2 | 12/2009 | Nygaard et al. | |
| 7,684,054 B2 * | 3/2010 | Crowther | G01B 11/2433 356/426 |
| 7,738,088 B2 | 6/2010 | Spalding | |
| 7,738,121 B2 | 6/2010 | Spalding | |
| 7,755,754 B2 | 7/2010 | Spalding | |
| 7,777,900 B2 | 8/2010 | Nygaard et al. | |
| 7,796,278 B2 | 9/2010 | Spalding et al. | |
| 7,812,970 B2 | 10/2010 | Nygaard | |
| 8,054,460 B2 | 11/2011 | Agapiou et al. | |
| 8,179,434 B2 | 5/2012 | Koval et al. | |
| 8,416,403 B2 * | 4/2013 | Nygaard | G01B 11/08 356/239.4 |
| 8,570,504 B2 | 10/2013 | Nygaard | |
| 8,723,068 B2 | 5/2014 | Nygaard | |
| 2003/0039388 A1 | 2/2003 | Ulrich et al. | |
| 2003/0201211 A1 | 10/2003 | Bennett et al. | |
| 2004/0022427 A1 | 2/2004 | Yang et al. | |
| 2004/0066505 A1 | 4/2004 | Berg et al. | |
| 2004/0223143 A1 | 11/2004 | Yasuda et al. | |
| 2004/0263957 A1 * | 12/2004 | Hirahara | A01H 4/006 359/372 |
| 2005/0174567 A1 | 8/2005 | Hanna | |
| 2006/0236792 A1 | 10/2006 | Hanna | |
| 2008/0013820 A1 | 1/2008 | Vertoprakhov et al. | |
| 2008/0049235 A1 | 2/2008 | Crowther | |
| 2009/0103107 A1 | 4/2009 | Nygaard | |
| 2009/0103111 A1 * | 4/2009 | Spalding | G01B 11/245 356/638 |
| 2009/0103112 A1 | 4/2009 | Nygaard | |
| 2009/0279083 A1 * | 11/2009 | Agapiou | G01N 21/954 356/241.1 |
| 2010/0201806 A1 | 8/2010 | Nygaard et al. | |
| 2010/0245850 A1 | 9/2010 | Lee et al. | |
| 2012/0105429 A1 | 5/2012 | Nygaard | |
| 2012/0293623 A1 | 11/2012 | Nygaard | |
| 2012/0293789 A1 | 11/2012 | Nygaard | |

FOREIGN PATENT DOCUMENTS

| | | |
|---|---|---|
| WO | 2005022076 A2 | 3/2005 |
| WO | 2009130062 A1 | 10/2009 |

OTHER PUBLICATIONS

International Preliminary Report on Patentability; International application No. PCT/US2012/037892; date of issuance of report Nov. 19, 2013.

Extended European Search Report, related European application No. 12786466.8; dated Feb. 16, 2015.

Notice of Allowance and Fee(s) Due; related U.S. Appl. No. 14/876,187; date mailed: Mar. 15, 2016.

Extended European Search Report; related EP application No. 13757558.5; date of completion of search Sep. 1, 2015.

Notice of Allowance and Fee(s) Due; related U.S. Appl. No. 14/876,192; date mailed Mar. 31, 2016.

\* cited by examiner

NON-CONTACT METHOD AND SYSTEM FOR INSPECTING A MANUFACTURED PART AT AN INSPECTION STATION HAVING A MEASUREMENT AXIS

CROSS-REFERENCE TO RELATED APPLICATIONS

This application is a continuation-in-part of U.S. patent application Ser. No. 14/050,907, filed Oct. 10, 2013, which is a continuation of U.S. patent application Ser. No. 13/109,369, filed on May 17, 2011, now U.S. Pat. No. 8,570,504. This application is also a continuation-in-part of U.S. patent application Ser. No. 13/414,081 filed on Mar. 7, 2012.

TECHNICAL FIELD

This application relates to non-contact methods and systems for inspecting manufactured parts such as ammunition cases and threaded fasteners.

Overview

Traditional manual, gauging devices and techniques have been replaced to some extent by automatic inspection methods and systems. However, such automatic inspection methods and systems still have a number of shortcomings associated with them.

Many parts, such as fasteners and ammunition cartridges and cases develop cracks, splits, or other outer surface defects during the manufacturing process. While parts can be linearly moved along their axes during the inspection process, this adds additional time to the process.

In optical metrology, inter-reflection (i.e., double bounce or secondary reflection) poses a challenge for surface measurement of shiny objects. Due to specular reflections that can occur among concave surfaces or combinations of surfaces positioned near right angles to each other, the true desired laser lines are often obscured by inter-reflection lines. Such obscuration makes it difficult to measure shiny surfaces of complex surface geometry.

Laser triangulation measuring equipment generally operate by projecting, with a laser beam having a wavelength centered at approximately 830 nm (infrared (IR) radiation), a light spot having a preset spot size onto the surface to be examined, e.g., from a laser projection "gun" that may be mounted normal to the surface being examined. A light detection unit including a lens and a light detecting element or "camera," such as a CCD or CMOS imaging chip or a position sensing device (PSD), e.g., of silicon, at an offset angle to the projection axis may observe the position of the laser spot in its field of view and output a signal describing the angle at which the spot appeared in the field of view. The range to the object can be computed from the angle information when the distance between the laser projection axis and the light detection unit is known. The offset angle between the laser beam and the line of sight of the light detection unit is often referred to as the "triangulation angle." Based on which part of the detector the light reflected from the imaged object impinges, the height or "z-component" of the object at the point at which the light spot impinges upon the object may be determined.

Inspection of defects on and in small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the U.S. Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

FIG. 1a is a side schematic view of a .50 caliber case. As explained in the above-noted military standard, a case is counted as a defective because of a split case if the cartridge case shows a definite separation of the metal entirely through the case wall. A case is classified as either a "major" or "critical" defect depending on the location of split. A split in the (I), (S) or (J) position is counted as a "major" defect when no loss of powder occurs; and as a "critical" defect when loss of powder occurs. A split in the (K), (L) or (M) position is counted as a "critical" defect.

FIG. 1b is a side schematic view of a .30 caliber case. As noted above, a case is counted as a defective because of a split case if the cartridge case shows a definite separation of the metal entirely through the case wall. A case is classified either as "major" or "critical" defective depending on location of split. A split in the (I) of (J) position is counted as a "major" defect when no loss of powder occurs; and as a "critical" defect when loss of powder occurs. A split in the (K), (L), or (M) position is counted as a "critical" defect.

FIG. 1c is a side schematic view of a .45 caliber case. Again, as noted above, a case is counted as defective because of a split case if the cartridge case shows a definite separation of the metal entirely through the case wall. A case is classified either as a "major" or "critical" defective depending on the location of the split. A split in the (I) or (J) position is counted as a "major" defect when no loss of powder occurs; and as a "critical" defect when loss of powder occurs. A split in the (K), (L), or (M) position is counted as a "critical" defect.

U.S. Pat. No. 4,923,066 discloses an automatic visual inspection system for small arms ammunition which sorts visual surface flaws at high speed according to established standards which can be tailored to fit specific needs.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact laser-based sensor guided by a precision mechanical system to scan a thread form producing a set of digitized images of the thread form.

WO 2009/130062 discloses a method and a device for the optical viewing of objects.

As described in U.S. Pat. No. 6,098,031, triangulation is the most commonly used 3-D imaging method and offers a good figure of merit for resolution and speed. U.S. Pat. Nos. 5,024,529 and 5,546,189 describe the use of triangulation-based systems for inspection of many industrial parts, including shiny surfaces like pins of a grid array. U.S. Pat. No. 5,617,209 shows a scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability.

U.S. Pat. No. 5,098,031 discloses a method and system for high-speed, 3-D imaging of microscopic targets. The system includes confocal and triangulation-based scanners or subsystems which provide data which is both acquired and processed under the control of a control algorithm to obtain information such as dimensional information about the microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The triangulation-based subsystem also includes a detector of electromagnetic radiation which is placed at a second location which is non-collinear with respect to the incident beam. Digital data is derived from signals produced by the detectors.

U.S. Pat. No. 5,815,275 discloses triangulation-based 3-D imaging using an angled scanning beam of radiant energy.

Published U.S. Patent Applications 2009/0103107 and 2009/0103112 disclose part inspection using a profile inspection subsystem and triangulation.

U.S. Pat. No. 4,547,674 discloses a method and apparatus for inspecting gear geometry via optical triangulation.

U.S. Pat. No. 4,970,401 discloses a non-contact triangulation probe system including a base plate and a first non-contact triangulation probe including a light source mounted on a first movable slide.

U.S. Pat. Nos. 5,168,458 and 5,170,306 disclose methods and systems for gauging threaded fasteners to obtain trilobular parameters.

Other U.S. patent documents related to the invention include: U.S. Pat. Nos. 3,411,009; 3,604,940; 4,280,624; 4,315,688; 4,598,998; 4,636,635; 4,644,394; 4,691,231; 4,852,983; 4,906,098; 4,912,318; 4,923,066; 4,969,746; 5,521,707; 5,608,530; 5,646,724; 5,291,272; 6,055,329; 4,983,043; 3,924,953; 5,164,995; 4,721,388; 4,969,746; 5,012,117; 6,038,521; 7,329,855; 7,738,121; 6,055,329; 7,065,242; 8,723,068; 7,684,054; 7,403,872; 7,633,635; 7,312,607; 7,777,900; 7,633,046; 7,633,634; 7,738,121; 7,755,754; 7,738,088; 7,796,278; 7,684,054; 8,054,460; 8,179,434 and U.S. published patent applications 2010/0245850, 2010/0201806, 2012/0293623; 2012/0105429; and 2012/0293789.

SUMMARY OF EXAMPLE EMBODIMENTS

An object of at least one embodiment of the present invention is to provide a high-resolution, low-cost method and system for inspecting a manufactured part at an inspection station having a measurement axis by rotating the part.

In carrying out the above object and other objects of at least one embodiment of the present invention, a method of inspecting a manufactured part at an inspection station having a measurement axis is provided. The method includes the step of supporting a part having opposite ends, a length between the ends, a width and a part axis. The part has backside and frontside surfaces when supported. The method also includes rotating the supported part about the measurement axis so that the part moves at predetermined angular increments during at least one rotational scan. The steps further include directing a backside beam of collimated radiation at substantially the entire backside surface of the supported part at each of a first plurality of consecutive angular increments of movement. The backside beam is occluded by the supported part at each of the first plurality of consecutive increments of movement to create a stream of unobstructed portions of the backside beam in rapid succession passing by and not blocked by the supported part. The steps include directing a frontside beam of radiation at at least a portion of the entire frontside surface of the supported part at each of a second plurality of consecutive angular increments of movement. The frontside beam is reflected by the supported part at each of the second plurality of consecutive increments of movement to create a stream of reflected portions of the frontside beam in rapid succession. The steps further include detecting the streams of reflected and unobstructed portions at the inspection station to obtain electrical signals and processing the electrical signals to determine at least one geometric dimension and any visual defects of the part.

Substantially the entire backside surface may be completely enclosed by a beam profile of the backside beam.

The beam profile may be generally rectangular with a height greater than or equal to the length of the part and a width greater than or equal to the width of the part.

The streams of reflected and unobstructed portions may be detected at a single image plane.

The part axis may be defined as being central to the part and parallel to its length.

The method may further include centering and aligning the part axis with the measurement axis.

The method may further include projecting focused lines of radiation at the frontside surface of the supported part during the at least one rotational scan to obtain reflected radiation and sensing the reflected radiation to obtain electrical signals.

The part may have a radially extending surface wherein the focused lines are angled with respect to the radially extending surface.

The focused lines of radiation at the frontside surface may be strobed.

The first and second plurality of consecutive angular increments may be coincident.

Further in carrying out the above object and other objects of at least one embodiment of the present invention, a system for inspecting a manufactured part at an inspection station having a measurement axis is provided. The system includes a fixture to support a part having opposite ends, a length between the ends, a width and a part axis. The part has backside and frontside surfaces when supported. The system also includes an actuator assembly to rotatably drive the fixture about the measurement axis at predetermined angular increments of movement during at least one rotational scan. A backside illumination assembly directs a backside beam of collimated radiation at substantially the entire backside surface of the supported part at each of a first plurality of consecutive angular increments of movement. The backside beam is occluded by the supported part at each of the first plurality of consecutive increments of movement to create a stream of unobstructed portions of the backside beam in rapid succession passing by and not blocked by the supported part. A frontside illumination device directs a frontside beam of radiation at at least a portion of the entire frontside surface of the supported part at each of a second plurality of consecutive angular increments of movement. The frontside beam is reflected by the supported part at each of the second plurality of consecutive angular increments of movement to create a stream of reflected portions of the frontside beam in rapid succession. A lens and detector assembly images and detects the streams of reflected and unobstructed portions at the inspection station to obtain electrical signals. At least one processor processes the electrical signals to determine at least one geometric dimension and any visual defects of the part.

Substantially the entire backside surface may be completely enclosed by a beam profile of the backside beam.

The beam profile may be generally rectangular with a height greater than or equal to the length of the part and a width greater than or equal to the width of the part.

The streams of reflected and unobstructed portions may be detected at a single image plane of the lens and detector assembly.

The part axis may be defined as being central to the part and parallel to its length.

The system may further include a part centering and aligning subsystem to center and align the part axis with the measurement axis.

The system may further include a triangulation-based sensor configured to project focused lines of radiation at the frontside surface of the supported part during the at least one rotational scan and to sense corresponding reflected lines of radiation to obtain electrical signals.

The part may have a radially extending surface wherein the focused lines are angled with respect to the radially extending surface.

The focused lines of radiation may be strobed.

The frontside illumination device may include an array of spaced light sources.

Each of the light sources may be a light emitting diode.

The light sources may be arranged in a generally curved arrangement.

The actuator assembly may include a stepper motor.

Other technical advantages will be readily apparent to one skilled in the art from the following figures, description and claims. Moreover, while specific advantages have been enumerated, various embodiments may include all, some or none of the enumerated advantages.

BRIEF DESCRIPTION OF THE DRAWINGS

For a more complete understanding of the present invention, and for further features and advantages thereof, reference is made to the following description taken in conjunction with the accompanying drawings, in which.

DETAILED DESCRIPTION OF EXAMPLE EMBODIMENTS

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In general, and as described below, at least one embodiment of the present invention provides a non-contact method and system for inspecting a manufactured part at an inspection station having a measurement axis. A first embodiment of the system is generally indicated at 10 in FIG. 3. A second embodiment of the system is generally indicated at 10' in FIG. 21. In general, parts of the two embodiments which are substantially the same in either structure or function have the same reference number but the parts of the second embodiment have a single prime designation. The part, such as a threaded fastener, has a length, a width, and a part axis which, preferably, is central to the part and parallel to its length.

Figure 1C:
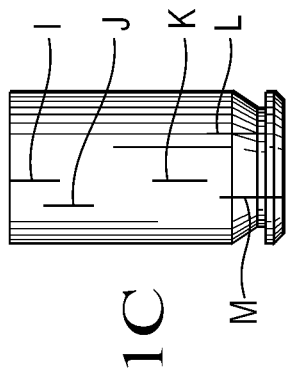
FIG. 1c is a side schematic view of a .45 caliber cartridge case.
Figure 1B:
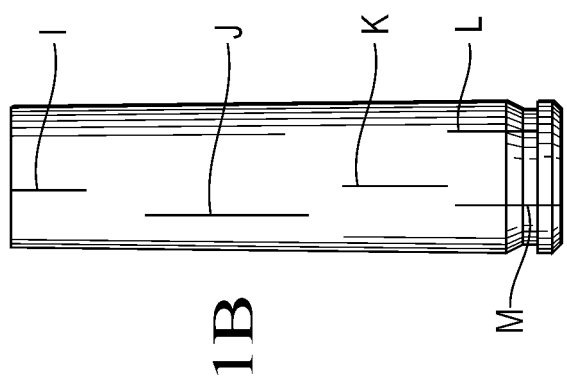
FIG. 1b is a side schematic view of a .30 caliber cartridge case.
Figure 1A:
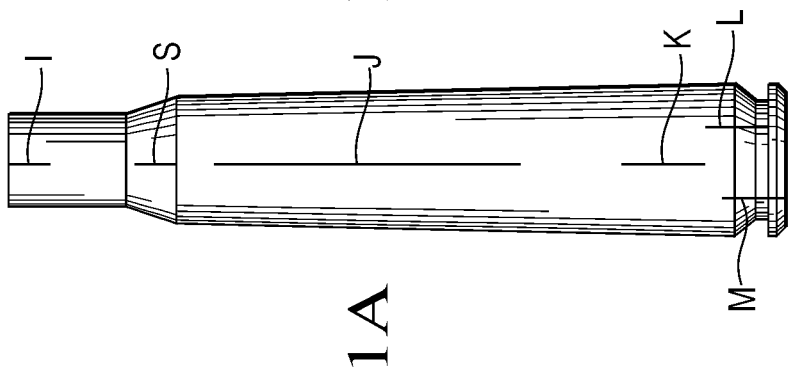
FIG. 1a is a side schematic view of a .50 caliber cartridge case.

Referring now to FIGS. 3, 12, 13, 14 and 16 a threaded bolt, generally indicated at 36, is held or supported by upper and lower parts 31 and 33, respectively, of a chuck or fixture, generally included at 32. In the second embodiment of FIG. 21 only a fixture 32' including a lower part or recess bit 33' is required. The lower part or recess bit 33 is mounted for rotary movement with a part stage 14 mounted above a top plate 42 of a base of the system 10. The part stage 14 is coupled via a coupler to the rotary output shaft 35 of an electric motor 28 supported below the plate 42. A head 37 of the bolt 36 is driven by the bit 33 which extends into the head 37 at one end surface thereof. This feature allows threads 38 as well as the entire exterior side surfaces of the bolt 36 to be optically inspected in an embodiment of the system 10 of the present invention. Other parts, such as the cases of FIGS. 1a-1c and a case generally indicated at 100 in FIG. 5 can be rotatably driven by the motor 28 via a motor driver controlled by a system controller (FIG. 12) while being held by upper and lower parts, generally indicated at 102 and 104, respectively, in FIGS. 4, and 7-9 and upper part 102 in FIGS. 10 and 11.

Figure 21:
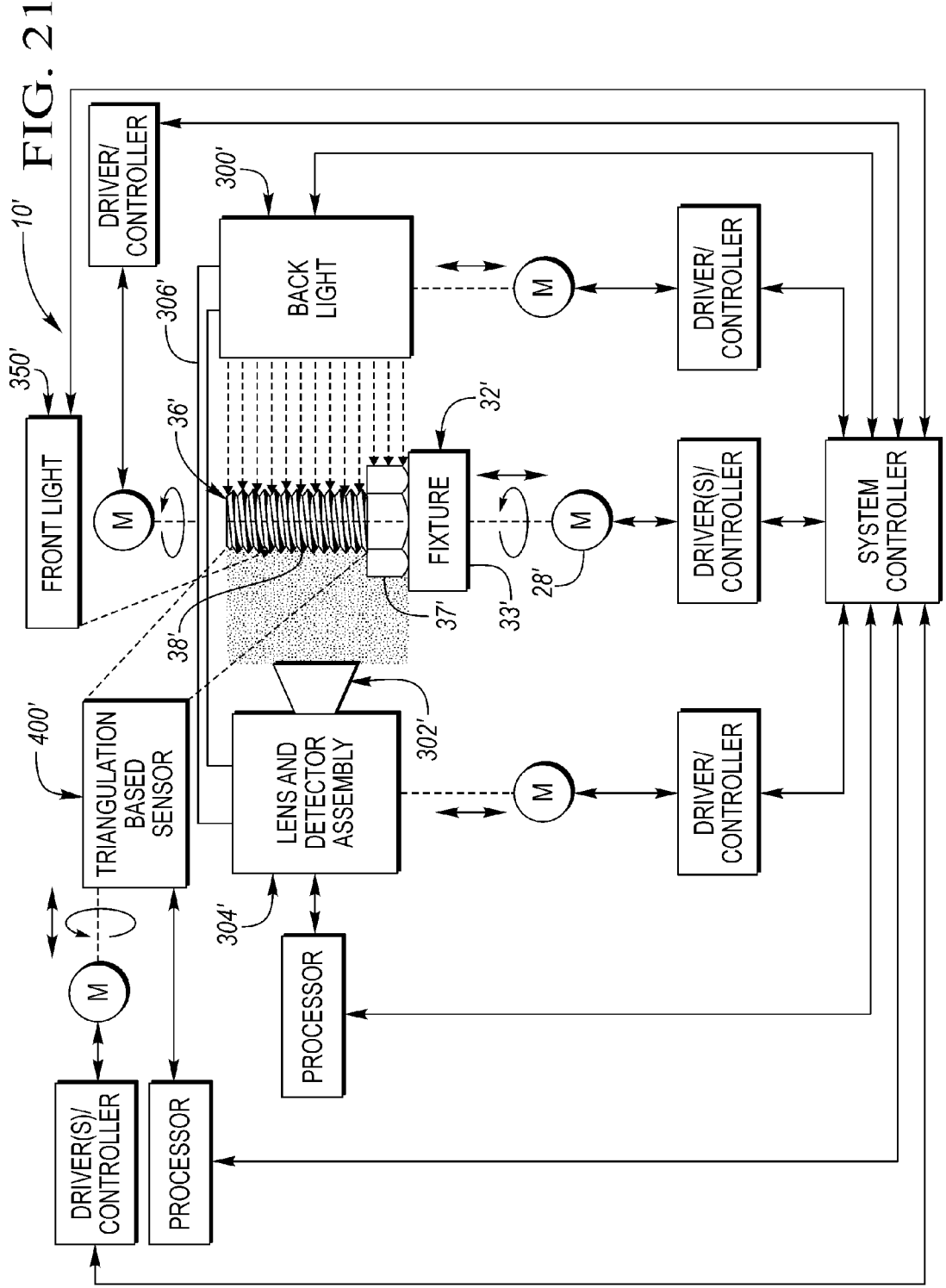
FIG. 21 is a block diagram schematic view that illustrates yet another embodiment of a non-contact method and system for inspecting parts.

In like fashion and referring to FIG. 21, the bolt 36' is rotatably driven by an actuator or motor 28' such as a stepper motor via a motor driver or motor controller upon receiving control signals from a system controller. The motor 28' either directly or via a transmission coupled to the output shaft of the motor 28' may also alternatively raise or lower the fixture 32' and the supported bolt 36' via a second motor driver or controller.

Figure 4:
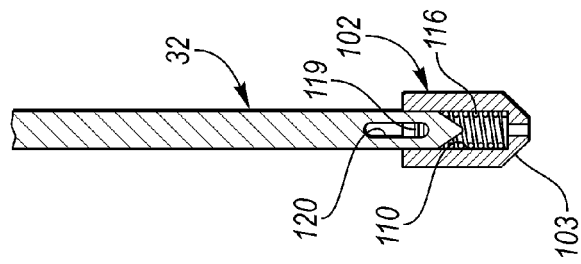
FIG. 4 is a side elevational view, partially and broken away and in cross-section, of an upper tooling unit including an upper holding device of FIG. 3.
Figure 3:
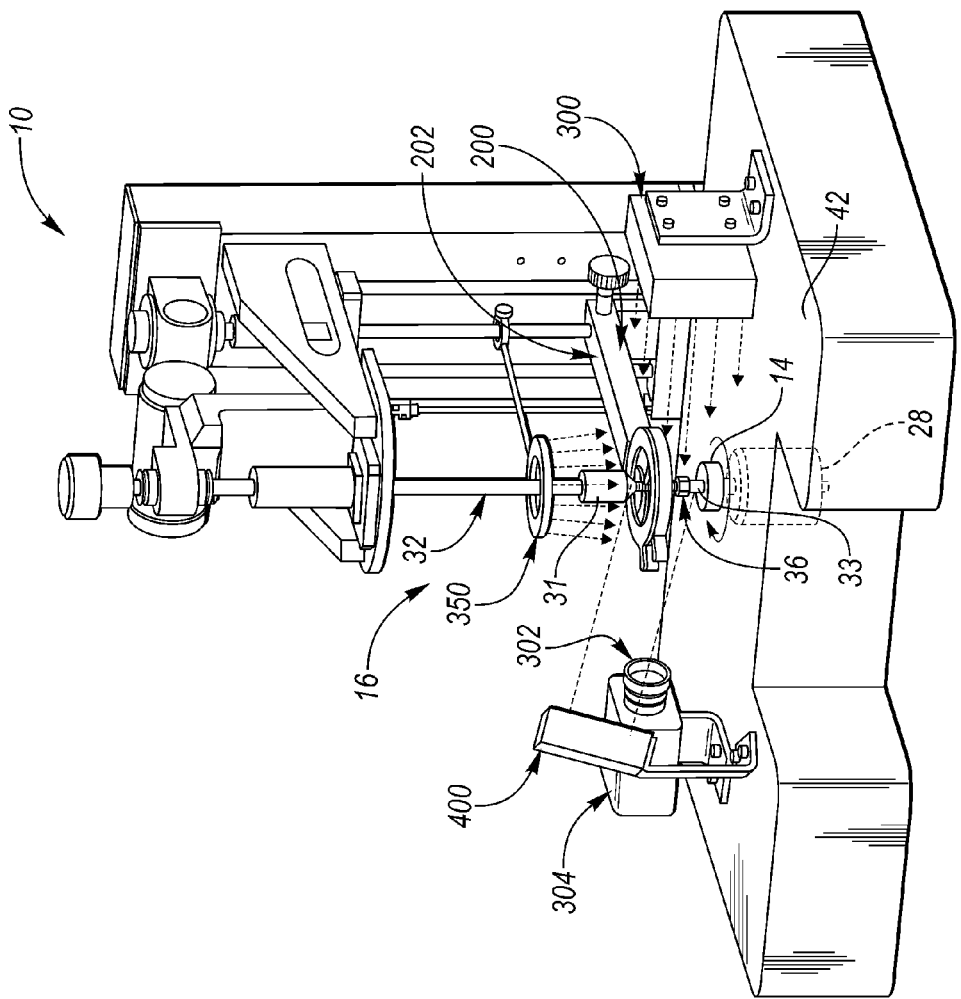
FIG. 3 is a schematic perspective view of an example embodiment of a system of the invention.
Figure 5:
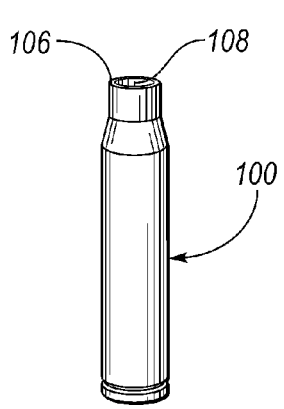
FIG. 5 is a front perspective view of cartridge case including an apertured top surface located at a mouth end of the case.
Figure 6:
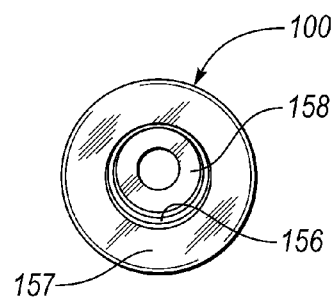
FIG. 6 is a bottom perspective view of an apertured bottom surface located at a primer end of the case.
Figure 7:
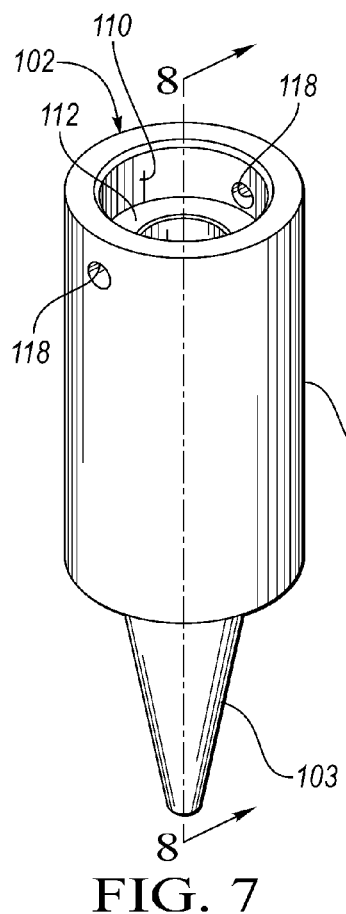
FIG. 7 is a side perspective view of an upper holding device constructed in accordance with one embodiment of the present invention.
Figure 8:
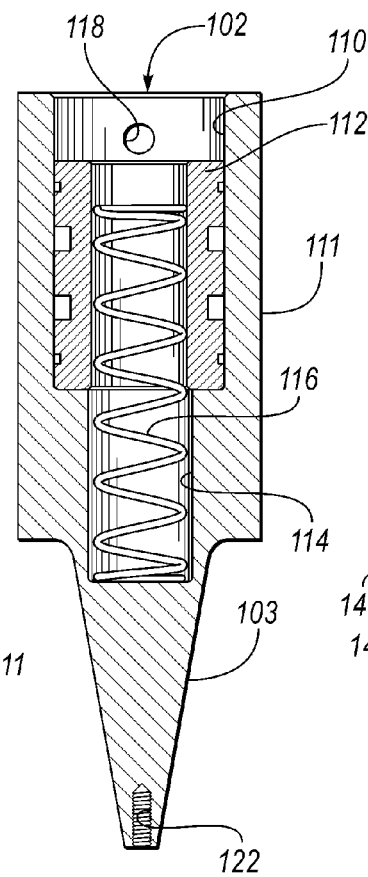
FIG. 8 is a side sectional view of the device of FIG. 7 taken along lines 8-8.
Figure 9:
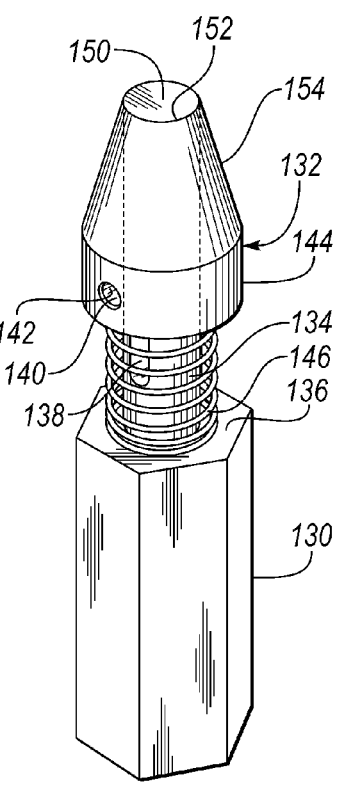
FIG. 9 is a side perspective view of a lower holding device also constructed in accordance with one embodiment of the present invention.

Referring to FIGS. 3 and 4, there is shown a schematic, side elevational view of an upper tooling unit 16 for bolts 36 and ammunition cases 100, respectively. The tooling unit 16 includes a rod 32 which is manually movable along a central axis of the rod 32 in up and down directions by an operator of the system 10. The upper tooling unit 16 (as described in detail in U.S. Pat. No. 8,004,694) includes the upper part 31 (for bolts) or the upper part 102 (for cases) and comprises a spring-loaded, upper holding device or tooling assembly. The upper part 102 has a tip portion 103 which retains a part such as the ammunition case 100 to be inspected at an upper, apertured end surface 106 of the case 100 by extending into an opening 108 in the case 100 (FIG. 5). The tip portion 103 is frustum-shaped and has a sloped region and a cross-sectional shape substantially identical to the shape of opening 108 in the end surface 106 at a mouth end of the case 100. The sloped region of the tip portion 103 defines a range of sizes of the opening 108 that can be measured at the measurement station.

The holding device 102 has a first central bore 110 formed in a cylindrical housing portion 111 and in which a cylindrical, hollow bearing 112 is disposed. The holding device 102 also has a second central bore 114 concentric with the first central bore 110 and in which a compression spring 116 is disposed within the hollow bearing 112. A hole 118 extends through an upper portion of the housing portion 111 to receive a dowel (119 in FIG. 4) by which the holding device 102 is secured to the lower end of the rod 32. The lower end of the rod 32 has an elongated slot 120 extending therethrough which receives and retains the dowel 119. The lower end of the rod 32 is received within the bore 110 and engages the top end of the spring 116 to compress the spring 116 within the bore 114.

A threaded hole 122 is typically provided at a distal end of the tip portion 102 to threadably receive and retain one of a number of possible tips (not shown) that can contact a surface of a part or case to be inspected.

Figure 10:
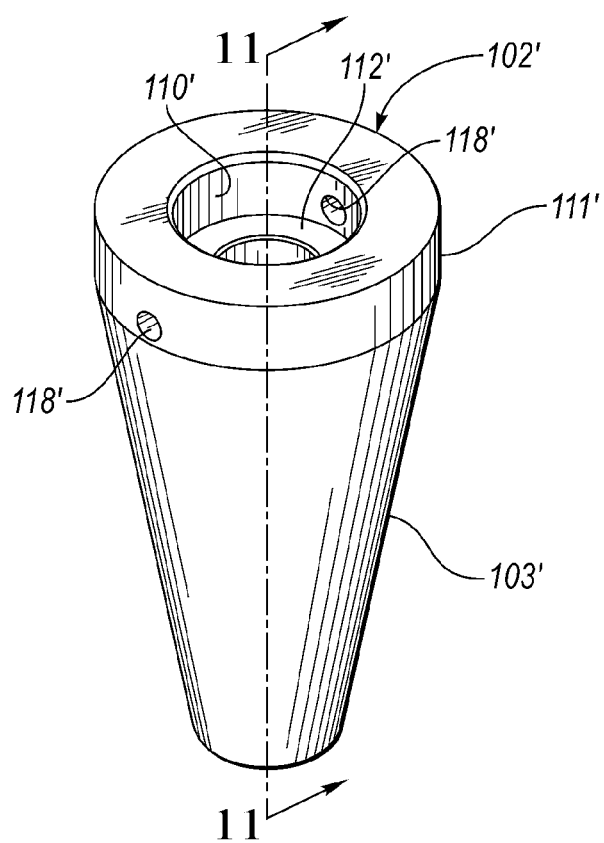
FIG. 10 is a side perspective view of an upper holding device constructed in accordance with another embodiment of the present invention.
Figure 11:
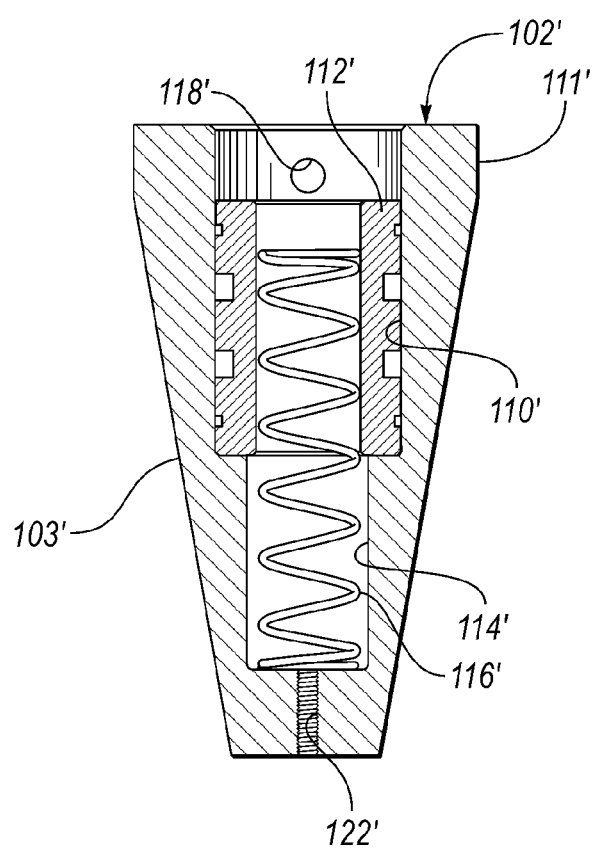
FIG. 11 is a side sectional view of the device of FIG. 10 taken along lines 11-11.

FIGS. 10 and 11 illustrate a second embodiment of an upper holding device, generally indicated at 102'. Parts of the upper holding device 102' which have the same or similar structure or function as the parts of the first embodiment (i.e., upper holding device 102) have the same reference number but have a prime designation. The upper holding device 102' generally is provided at the lower end of the rod 32 when measuring an opening in an ammunition case which is larger than opening that can be measured with the holding device 102.

A hexagonal base 130 (FIG. 9) of a lower holding device or tooling assembly, generally indicated at 132, is inserted into the part stage 14. The lower holding device 132 includes a pin 134 which extends upwardly from a top surface 136 of the base 130.

Much like the way the upper holding device 102 is secured to the rod 32, the pin 134 has an elongated aperture 138 which receives a dowel pin 140 which extends therethrough and through a hole 142 which extends through a cylindrical portion 144 of the lower holding device 132. A compression spring 146 extends between the top surface 136 and the lower surface of the cylindrical portion 144 to bias the cylindrical portion 144 away from the base 130.

A distal end portion 150 of the pin 134 extends through a central bore 152 which extends through a tip portion 154 of the lower holding device 132. The tip portion 154 is frustum-shaped and has a sloped region and a cross-sectional shape substantially identical to the shape of an opening 156 in an end surface 157 at a primer end of the case 100. The sloped region of the tip portion 154 defines a range of sizes of the opening 156 that can be measured at the measurement station. The distal end 150 of the pin 134 moves within the bore 152 after the sloped region of the tip portion 154 extends into the opening 156 of the case 100 and engages the side walls which define the opening 156. After engagement, further movement of the tip portion 154 downward against the biasing action of the spring 146 exposes the distal end 150 of the tip portion 154 which engages an inner end surface 158 of the opening 156. During this movement, the dowel pin 140 slides within the aperture 138 of the pin 134. As described herein, the depth of the primer pocket or opening 156 is determined after scanning the case 100 and the holding device 132. The depth that the pin 134 extends into the opening 156 and engages the end surface 158 is the depth of the opening 156.

In other words, the upper tooling for the case 100 incorporates a hollow cone (or frustrum) which lowers down inside the mouth of the case 100 and seats on the inner diameter of the mouth. This cone assembly is spring-loaded which provides a small preload to hold the part in place on the part stage 14 of the system 10. By defining a region that encompasses the point or line of contact between the cone and the case 100 and then measuring the minimum diameter in that region, the system 20 indirectly measures the inner diameter (ID) of the mouth.

If the ID on the part to be measured has a radius, the cone will seat deeper inside the mouth and the diameter measured will be larger than the actual ID of the part. In order to minimize this effect, the angle of the cone used in this fixture should be as shallow as possible. A cone with a shallow angle results in more accurate measurements.

Practically, a cone with a very shallow angle will tend to wedge itself inside the mouth of the part. The force of the spring 116 or 116' in the upper tooling assembly can cause the cone to become stuck inside the case which can make unloading parts from the system challenging. Furthermore, a very shallow cone angle can be used only on parts with a very narrow range of mouth IDs. A cone with a steep angle is less likely to get stuck inside the mouth of the part and is usable on a wider variety of part sizes.

In light of these considerations, a relatively shallow cone angle of 10° is preferred with two different cone designs, one for small caliber ammunition (50 cal and smaller) and one for medium caliber ammunition (20 mm and larger). This is a convenient break point because it is rare that a single company manufacturers both small and medium caliber ammunition.

The wall thickness is calculated by subtracting the directly measured OD from the indirectly measured ID and dividing this result by two.

The lower tooling uses a similar concept, with the exception that this tooling configuration also allows the depth of the recess (primer pocket) to be determined. The basis of this assembly is a small post whose height has been pre-measured and is stored in memory of the system. Surrounding this post is a cone which slides up and down on the post. This cone is constrained from coming off the post with a through-pin which rides in a slot cut into the post. This cone is biased from underneath by the spring 146.

When an ammunition case with a primer pocket fixture in the system 10, the ID of the primer pocket seats on the angled surface of the cone. The upper tooling presses the case down which, being seated on the cone, causes the spring 146 to compress until the base of the primer pocket comes to rest on the top of the tooling post.

When the part is scanned in this configuration, the primer pocket diameter is determined by measuring the minimum diameter at the point where the cone contacts the head of the case in the same manner the mouth ID is indirectly measured as described above. The depth of the primer pocket is measured by measuring the height of the case head (above the base of the post) and subtracting this from the known height of the tooling post.

The choice of angle for the lower tooling cone (i.e., frustrum) requires consideration of all the same factors as the upper tooling cone. One additional detail is the available depth of the part recess. It is desirable to design this lower tooling assembly so that it can be used to measure a wide variety of recess depths and diameters. A shallow cone angle severely limits the range of recess aspect ratios (diameter vs depth) that can be measured with a single tooling design. In order to accommodate most of the small caliber range, a comprise angle of 18° is preferred. This allows measurement of common primer pockets machined into cases sized 7.62 mm and smaller.

Referring again to FIGS. 3 and 12 and as described in U.S. Pat. No. 8,550,444, the system 10 also preferably includes a part centering and aligning subsystem, generally indicated at 200. The subsystem or apparatus 200 ensures that a part is centered in the system 10 and that the part is aligned with the measurement axis (Z-axis) without the need to measure any distances or angles. In other words, the apparatus 200 ensures that the part is properly placed or positioned in the system 10 prior to the part being held, for example, between the upper tooling unit and the part stage 14. The part may be a threaded part such as the threaded fastener 36 or the ammunition case 100.

As described in U.S. Pat. No. 8,550,444, the apparatus 200 includes a carrier which defines a part receiving cavity. The apparatus 200 also has a central axis substantially parallel to a measurement axis or Z-axis and including a plurality of members or levers having open and closed positions. The members having holding faces which are substantially equidistant from the central axis during movement between the open and closed positions. At least one of the members applies a force on an exterior side surface of a part, disposed between the holding faces during movement between the positions to reposition the part. The repositioned part is centered and aligned with respect to the measurement axis. The holding faces releasably hold the repositioned part in the holding position between the open and closed positions of the members.

The apparatus 200 also includes manually operable lever arms which are coupled to their respective relatively moveable spring-biased ring members of the carrier. Movement of one of the lever arms either towards or away from the other lever arm (depending on the biasing of the spring(s)) causes the members to move from their open position to their holding position against the part to center and align the part.

The system 10 also includes a movable stage subsystem, generally indicated at 202, coupled to the apparatus 200 for sliding the apparatus 200 relative to the repositioned part along the central axis in the open position of the members to allow the exterior side surface of the repositioned part to be measured. In turn, the slide/base unit moves the movable stage subsystem 202 up and down. A horizontal support member couples the subsystem 202 to the apparatus 200 to move the apparatus 200 along the central axis.

The system 10 further includes a mechanism which is coupled to one end of the support member for translating the support member and the apparatus 200 a limited extent relative to the subsystem 202 along the central axis. The mechanism includes a manually operable knob to operate the mechanism.

Referring again to FIGS. 3, 12, 13 and 14, the system 10 also includes a backside illumination assembly, generally included at 300. The system 10' includes a backside illumination assembly, generally indicated at 300' in FIG. 21.

The illumination assembly 300 (and the assembly 300') directs a beam of collimated radiation at substantially the entire backside surface of the held part at predetermined angular increments of movement of the held part about the measurement axis of the system 10 (or system 10') during the rotational scan. The beam is occluded by the held part at each increment of movement to create a stream of unobstructed portions of the beam in rapid succession passing by and not blocked by the held part.

Preferably, substantially the entire backside surface is completely enclosed by a beam profile of the beam. The beam profile is generally rectangular with a height greater than or equal to the length of the part and a width greater than or equal to the width of the part as show in FIGS. 12, 13 and 14.

Referring again to FIG. 21, the backside illumination assembly 300' is substantially the same as the illumination assembly 300. The assembly 300' may be movable up or down via a motor M driven or controlled by a driver/controller upon receiving a control signal from the system controller.

The illumination assembly or radiant source 300 (or assembly 300') illuminates an object such as an ammunition case or threaded bolt to be imaged, and a telecentric optical lens 302 (or lens 302' of FIG. 21) receives the radiation passing by and not blocked by the case or bolt and guides it towards an image plane 303 of the image acquisition device or detector, generally referred as 304 (or detector 304' of FIG. 21). The illumination assembly 300 is provided for illustrative purposes in FIG. 14. Consequently, the radiation source 300 (and the source 300') preferably comprises a LED emitter 311 including a plurality of LED emitter elements serving to emit radiation in either the visible or ultraviolet range. The LED emitter of the source 300 (or source 300') is preferably high power, capable of generating 100 optical mW or more for each emitting element. A lens 308 (FIG. 14) collimates the radiation.

As shown in FIG. 21, the back light 300' and the detector 304' may be coupled together by a yoke 306' to rotate together about the part 36' via a motor via a driver/controller upon receiving a command signal from the system controller.

An optical or optoelectronic device for the acquisition of images (for example the camera or telecamera 304 or 304') has the image plane 303 which can be, for example, an electronic sensor (CCD, CMOS). The case or bolt is received and retained at a predetermined position and orientation for optical inspection by the fixture 32 of the system 10 (or fixture 32' of system 10'). Preferably the device 304 (and the device 304') is a high resolution digital telecamera, having the electronic sensor 303 with individual pixels of lateral dimensions equal to or less than one or more microns.

Referring again to FIG. 21, the assembly 304' can be driven up and/or down by a motor via a driver/controller upon receiving an appropriate control signal from the system controller. Typically, movement of the assembly 304' and the backlight 300' is coordinated by the system controller so that they move in unison.

The lens 302 (and the lens 302') schematically comprises a forward set of optical elements 305 proximal to the bolt or case, a rear optical element 306 proximal to the acquisition device 304 and an aperture diaphragm 307 interposed between the forward and rear sets of optical elements 305 and 306, respectively. The aperture diaphragm 307 comprises a circular window 308 transparent to the radiation, which is referred to as a diaphragm aperture. For example, the aperture diaphragm 307 can comprise an opaque plate preferably of thickness of a few tenths of a millimeter, and the diaphragm aperture can be defined a simple hole in the plate.

The diaphragm aperture or window 308 is coaxial to the optical axis 309 of the forward set of optical elements 305, and positioned on the focal plane of the forward set 305 defined for the wavelength range of radiation emitted by the radiant source 300.

The position of the focal plane of a set of optical elements mostly depends on the refraction index of the material from which the lenses are made, which, in turn, depends on the wavelength of the electromagnetic radiation passing through the lenses.

The lens 302 (and lens 302') only accepts ray cones 301 exhibiting a main (barycentric) axis that is parallel to the optical axis 309 of the forward set 305. Thereby, the lens 302 is a telecentric lens configured for the particular radiation. The rear set of optical elements 306 serves to compensate and correct the residual chromatic dispersion generated by the forward set optical elements 305 for the wavelength in question.

Figure 15:
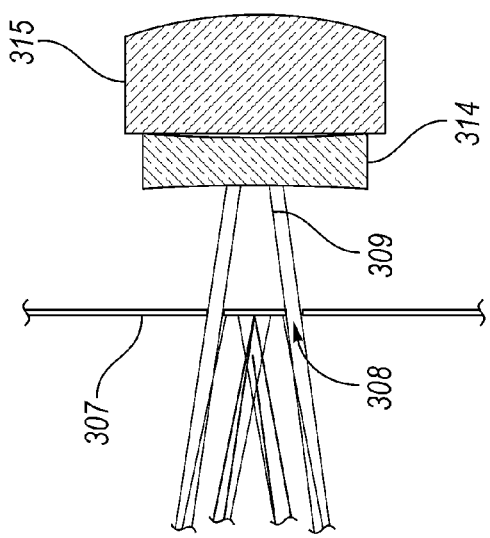
FIG. 15 is an enlarged view, partially broken away and in cross section, of a portion of the telecentric lens of FIG. 14 with corresponding rays of the radiation either blocked or passing therethrough the diaphragm.
Figure 16:
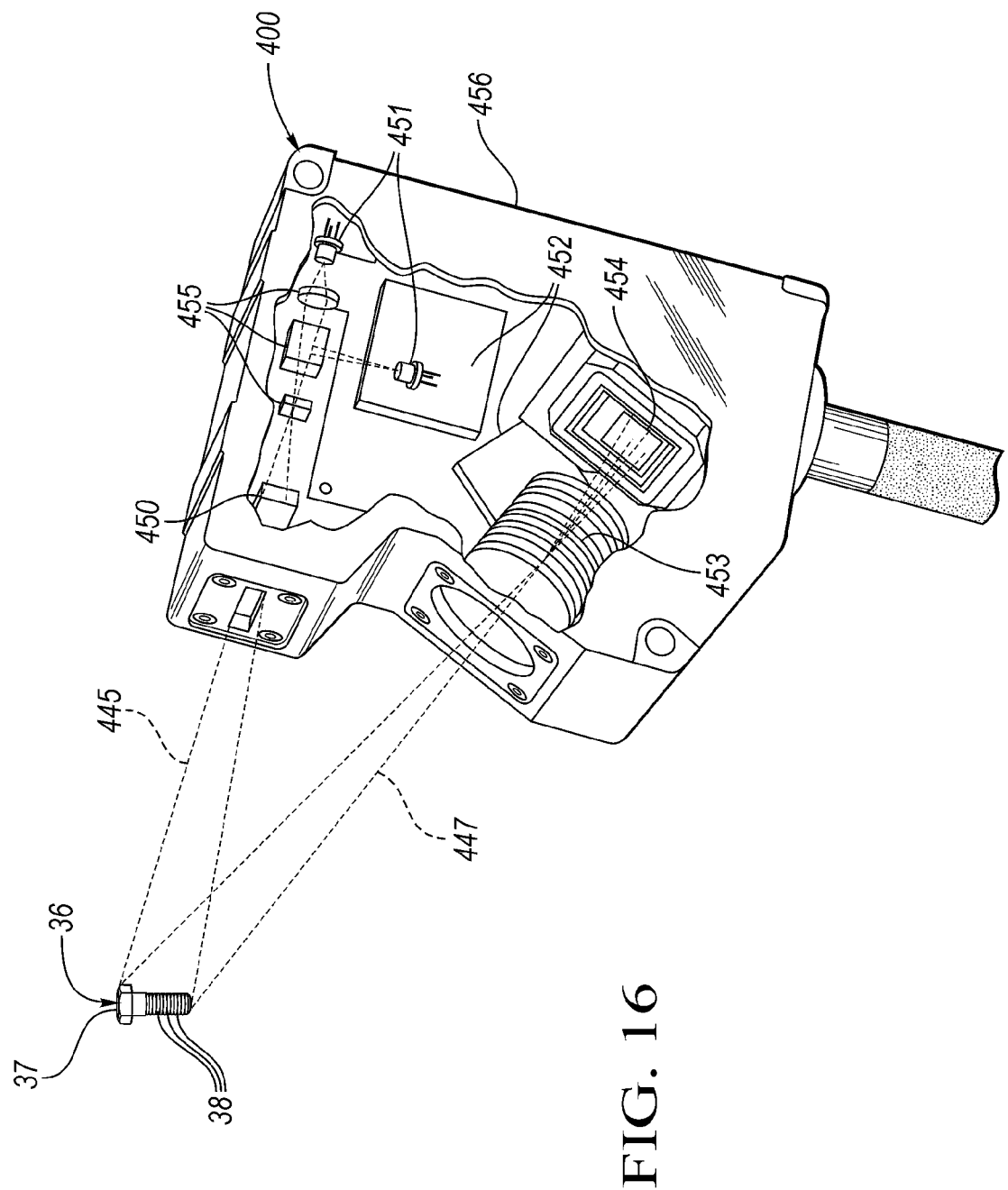
FIG. 16 is a schematic perspective view (partially broken away) of the various components of a sensor head of one embodiment of the system together with a threaded part.
Figure 17:
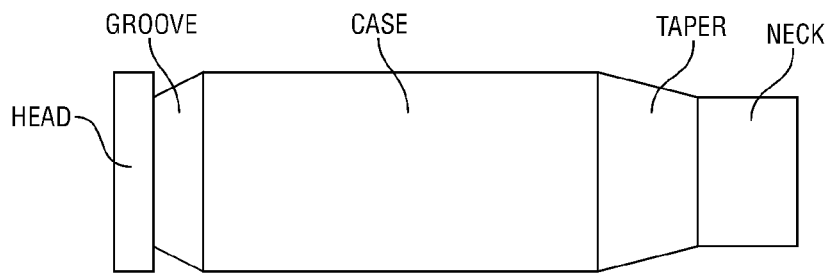
FIG. 17 is a schematic view wherein a framework in the figure is applied to a part such as a cartridge case once it has been located.
Figure 18:
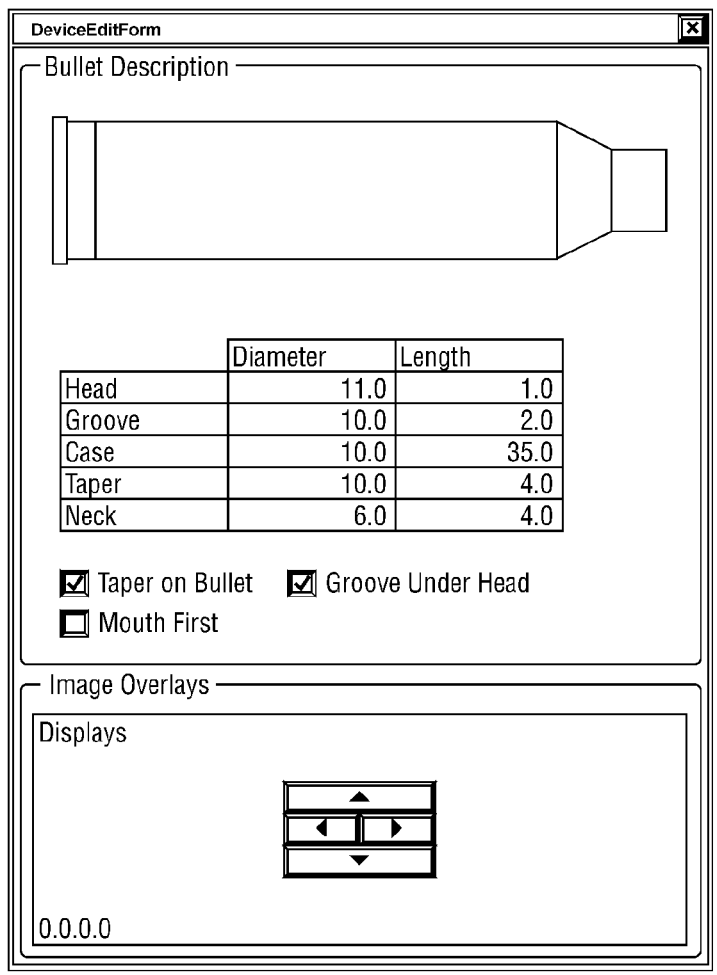
FIG. 18 is a schematic view of a screen shot which describes a cartridge case or bullet to be inspection.
Figure 19:
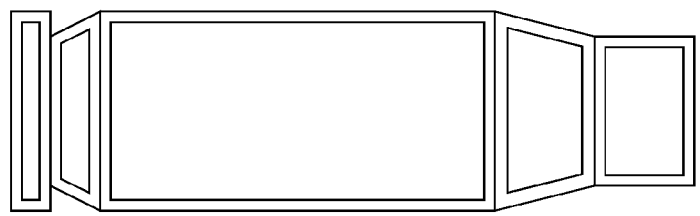
FIG. 19 is a schematic view, similar to the view of FIG. 17, wherein buffers are applied once the case regions have been identified.
Figure 20:
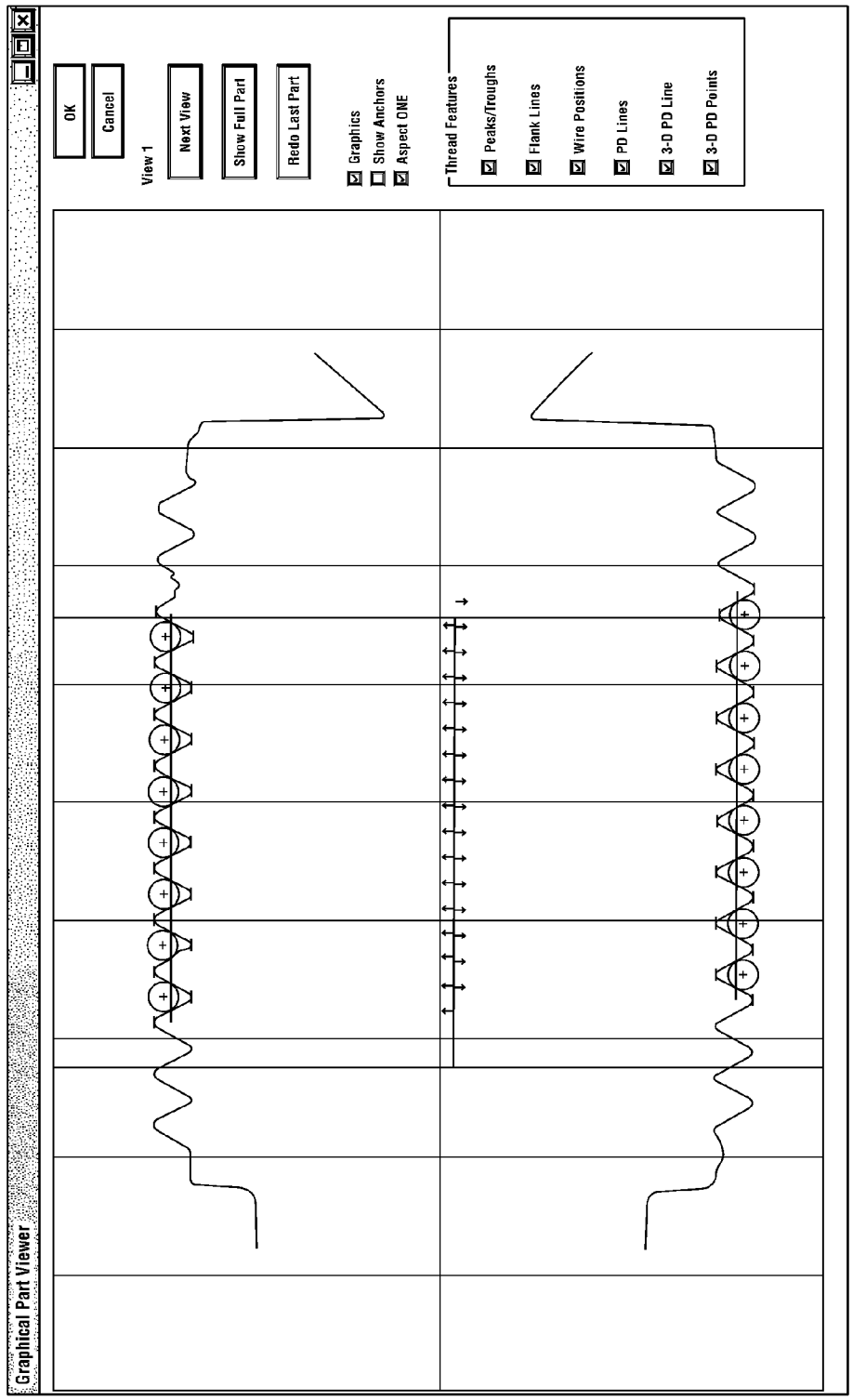
FIG. 20 is a screen shot of a graph of data with external wires with respect to a view of a threaded fastener.

The optical axis of the rear set 306 coincides with the optical axis 309 of the forward set 305 and the focal plane of the rear set 306 defined for the wavelength cited above, coincides with the plane on which the aperture diaphragm 307 is located. Consequently, rays of radiation 309 (FIG. 15) conveyed by the rear set 306 towards the image plane 303 form light cones, the main (barycentric) axis of which is parallel to the optical axis 309 of the lens 302 (and the lens 302').

The forward set 305 preferably includes two positive lenses, 312 and 313, which can exhibit a flat-convex, bi-convex, or meniscus shape. The positive lenses 313 and 312 can both be made in common optical glass. For example, they can both be made in low chromatic dispersion crown glass, including, for example, Schott glass varieties classified with codes N-SK16, N-BK7, or B270.

The rear set of optical elements preferably comprises four lenses respectively numbered from 314 to 317. The lens 314 which is proximal to the diaphragm 307 can be a negative lens serving to partially or completely correct the chromatic aberrations generated by the forward set 305. The negative lens 314 can be bi-concave, flat-concave, or meniscus shaped, and can be made of common optical glass, for example it can be made of high chromatic dispersion flint glass, for example, Schott optical glass types classified with codes N-F2, LLF1, or N-SF1.

The rear lenses 315, 316 and 317 are positive lenses that can all be made of common optical glass, for example in low chromatic dispersion crown glass, including the hereinabove cited Schott optical glass types classified with codes N-SK16, N-BK7, or B270.

The lens 302 (and the lens 302') is therefore both telecentric on the object side and telecentric on the image side, and overall the lens 302 is a bi-telecentric lens configured for light such as visible light or ultraviolet light.

Referring now to FIGS. 3, 12, 13 and 16, there is illustrated a triangulation-based sensor head, generally indicated at 400. The system 10' includes a sensor head 400' substantially the same as the sensor head 400. The sensor head 400 may comprise a high-speed, 2D/3D laser scanner (LJ-V7000 series) available from Keyence Corporation of Japan. Such a sensor head from Keyance generates a laser beam that has been expanded into a line and is reflected from the side surface of the part as well as any radially extending surfaces of the part, such as the threaded bolt 36. The reflected line of light 447 is formed on a HSE3-CMOS sensor 454 and by detecting changes in the position and shape of the reflection, it is possible to measure the position of various points along the surface of the part.

The sensor head 400' of FIG. 21 may rotate and/or linearly move via a motor via a rotary driver/controller and/or a linear driver/controller, respectively, upon receiving command signals from the system controller. A transmission (not shown) may convert the rotary motion of the motor output shaft to linear motion.

The sensor head 400 typically includes (FIG. 16) a cylindrical lens 450, at least one and preferably two semiconductor laser diodes 451, a GP64-Processor 452, a 2D Ernostar lens 453 and the HSE3-CMOS Sensor 454. Preferably, the laser diodes 451 emit "blue" light beams which are polarized and combined by optical elements or components 455 to form the line of laser light 445.

Preferably, the beams from the pair of blue laser diodes 451 are combined such that the transmitted beam is polarized in both X and Y axes. The captured images at the sensor 454 in both polarizations are used to generate a resulting 2D profile signal wherein stray reflections are cancelled.

As the bolts or cases rotate corresponding sets of 2D profile signals are generated by the sensor head 400. At least one processor processes the sets of 2D profile signals to obtain a 3D view of the complete side surface and any radially extending surfaces of the part.

The system controller provides control signals based on the signals from rotary sensors or encoders. Alternatively, sensors and/or encoders are not required if stepper motor(s) are provided. Alternatively or additionally, the signals from the rotary encoders are directly utilized by the sensor heads 400 at the station to control the sensor head 400. The control signals are utilized to control the sensor head 400 which preferably have encoder inputs which allow precise control over the position of 2D profile signals samples.

At least one signal processor may process the sets of 2D profile signals to identify a defective part as described in greater detail hereinbelow. The at least one processor may process the sets of 2D profile signals to obtain one or more measurements of the part.

A comparison of such a sensor head 400 with a 3D measurement camera reveal the following:

1. Easy Installation

When using a 3D camera, the laser light source and receiver (camera) are independent of each other, greatly complicating on-site installation and adjustment. With such sensor heads 400, the laser light source and receiver are contained in a single body or enclosure 456, making transmitter-to-receiver mounting adjusting unnecessary. This also ensures that the transmitter and receiver maintain this alignment regardless of machine use.

2. No Linearization Required

When using a 3D camera, the height of individual pixels and pixel pitch vary due to the relative positions of the laser light source and the receiver, requiring on-site linearization following installation. With such sensor heads 400, the output data is pre-linearized by the on-board controller (not shown) of the sensor head 400 without the need for additional post-processing.

3. Out of the Box Traceability

Because each such sensor head 400 is not a machine vision camera, but a traceable measurement device, traceability and calibration documentation is available out of the box. All such devices are factory calibrated to international traceability standards and compliance documentation is readily available.

Figure 2A:
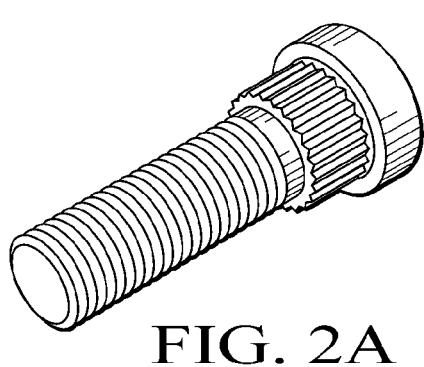
FIGS. 2a-2e are schematic views, of various threaded fasteners having various symmetric and non-symmetric features which can be extracted and measured using at least one embodiment of the present invention.
Figure 2B:
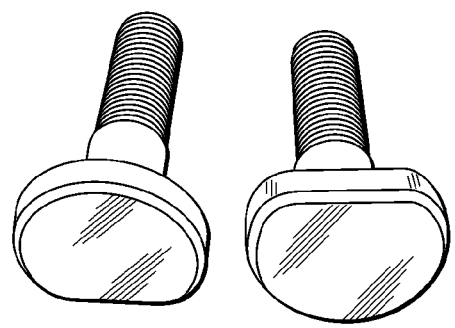
Figure 2C:
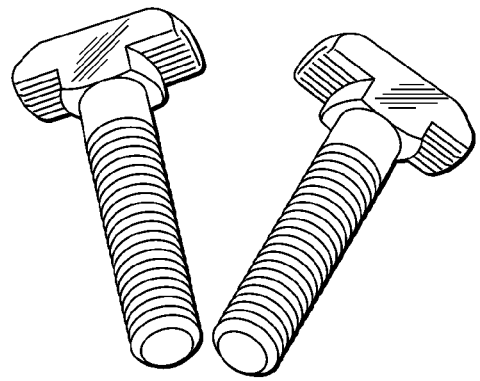
Figure 2D:
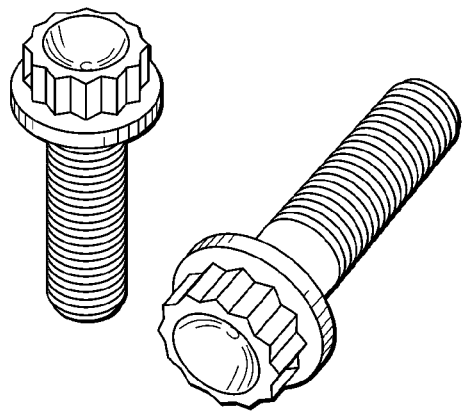
Figure 2E:
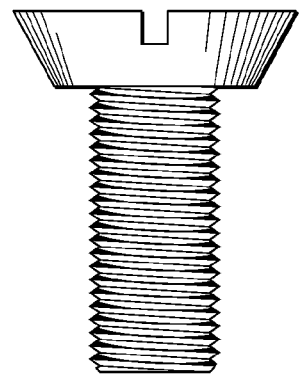

The sensor heads 400 and the at least one processor can extract serrations (FIG. 2a), knurls, twelve point aerospace (FIG. 2d) or non-symmetric features of part like D-head (FIG. 2b) or T-head (FIG. 2c) bolts etc. The operator may tell the system controller (FIG. 12) via a display and user interface where the interesting parameters are located on the Z axis (height of the part). Then, the software tools extract and measure features from the images and resulting 2D profile signals created by the reflected lines of radiation.

The 2D profile signals may be processed by the at least one processor under system control to obtain a 360 degree panoramic composite view or image which is used by the processor to determine at least one of a dent, a split, a perforation, a crack, a scratch, a wrinkle, a buckle, a bulge, and a surface blemish located at the side surfaces of the part where the part is an ammunition case.

The frontside illumination device of the first embodiment may include a ring LED illuminator 350 (FIGS. 3 and 12) and the frontside illumination device of the second embodiment may include a ring LED illuminator 350'. Each illuminator 350 and 350' includes a curved array of LED light sources, groups of which are under control of the system controller to provide direct illumination of the front of the case or bolt and are used to enhance defects in the front surface of the case or bolt. Alternatively, the frontside illumination device may be side-mounted so that the front light comes from the side of the part and not from above the part, i.e., basically like painting a thin line along the length of the part.

The detected optical images are processed by the image processor to determine at least one of a dent, a split, a perforation, a crack, a scratch, a wrinkle, a buckle, a bulge, and a surface blemish located at the side surfaces of the case.

Data/Image Processor for the Detection of Surface Defects on Small Manufactured Parts This vision system is especially designed for the inspection of relatively small manufactured parts such as threaded fasteners and small and medium caliber ammunition. The processing of images of the cartridge cases to detect defective cases is generally described in issued U.S. Pat. No. 7,403,872 as follows.

Dent Detection

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this theory. One option is to orient the light source so that light reflected off the part exterior is aimed directly into the camera aperture. Light which reflects off a dented region will not reflect bright background. Alternatively, the light source can be positioned with a shallower angle to the part. This will result in a low background illumination level with dents appearing as well deemed origin spots on the image.

The vision system detects dents on parts with multiple tapered sections. In particular, a bright background is created in highly tapered regions (with dents appearing as dark spots) while a dim background is created in flatter regions (with dents appearing as bright spots).

As previously mentioned, the vision system has two types of lights, each of which can be independently adjusted in order to properly illuminate a given taper.

Perforation Detection

Detecting perforations uses both of the principles outlined above. The task is much simpler however, as the region containing the defect is completely non-reflective. Therefore, perforations are visible as dark spots on surfaces illuminated by either shallow or steep angle illumination.

Software

Because the part is essentially at a pre-defined location and orientation when the images are acquired, the software need not auto-locate the part and identify regions of interest using preset visual clues.

Defect detection in each region of interest is typically conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Part Location

Previously locating the part in the image may be accomplished by running a series of linear edge detection algorithms. This algorithm uses variable threshold, smoothing and size settings to determine the boundary between a light and dark region along a defined line. These three variables are not generally available to the user, but are hardcoded into the software, as the only time they will generally need to change is in the event of large scale lighting adjustments.

The software first uses the above edge detection algorithm to find the back (left) end of the part in the image.

Once the left edge of the part has been located, the software runs four more edge searches along the top and bottom edges of the part.

Once the top and bottom edges of the part have been located, the midpoints of the edge pairs are calculated and joined in order to find the centerline.

The centerline search is then performed again, but rather than conducting the linear edge detections in the vertical direction, they are conducted perpendicular to the newly found centerline. This iteration reduces the small angle error associated with any potential misalignment of the part in the field of view.

A new centerline found using the results of the repeated top and bottom edge search.

Finally, the left edge is again located, this time along the new centerline. This action locates the very center of the left-hand edge of the part.

Part Regions

Once the part has been located in the image, a framework of part regions is defined using a hard-coded model of the anticipated part shape. In the case of ammunition, the regions defined by the framework include head, extractor groove, case, taper, and neck. Each of these regions can be varied in length and width through the user interface in order to adapt the software to varying case sizes. Note that although regions can be adjusted in size, they cannot have their bulk shape changed. A checkbox allows the taper and neck regions to be removed in order to inspect pistol cases (which do not have a taper). The size of the region framework as well as the state of the Taper/No-Taper checkbox is saved in the part profile. FIG. 11 shows the definition of the various regions on the part.

Figure 12:
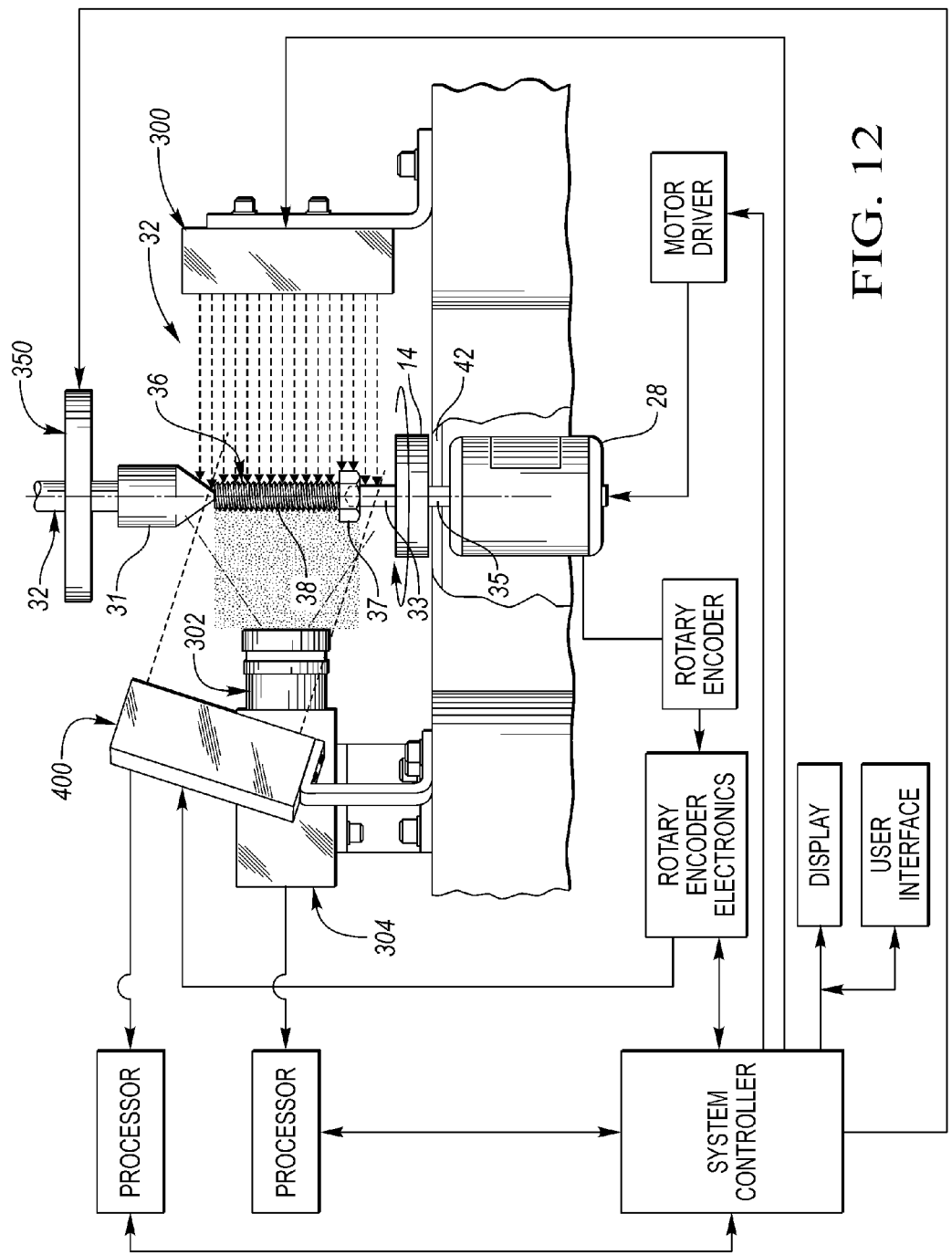
FIG. 12 is a side view, partially broken away, of the system of FIG. 3 together with a block diagram of various electronics of the system and showing the height of the collimated beam of radiation.
Figure 13:
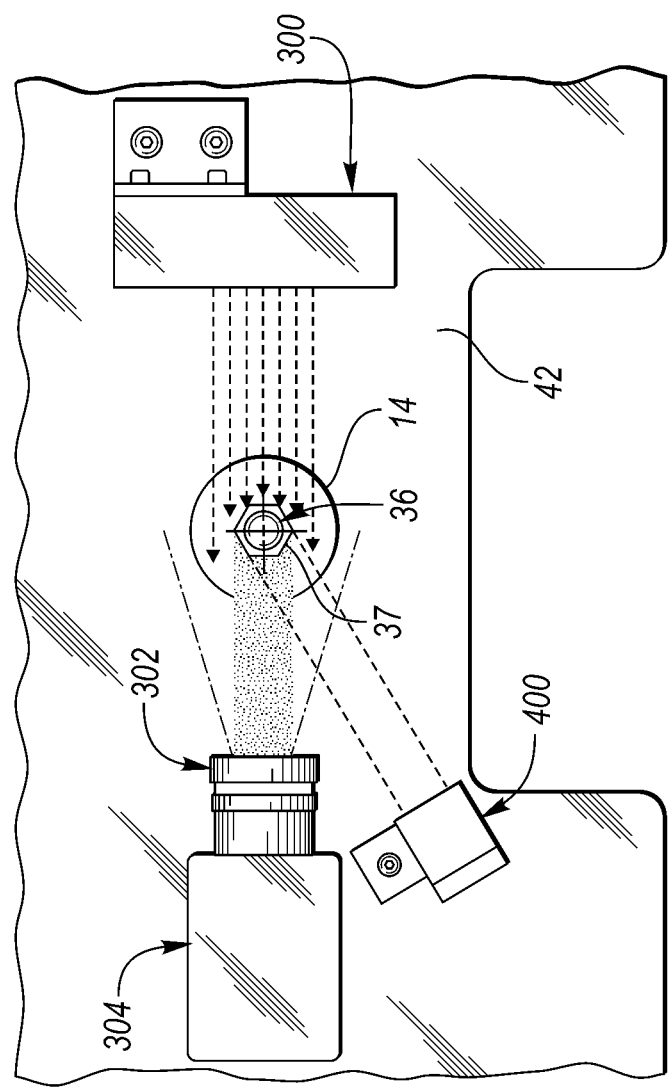
FIG. 13 is a top plan schematic view, partially broken away, of parts of the system of FIGS. 3 and 12 and showing the width of the collimated beam of radiation.

This region definition is shown in screenshot of FIG. 12. Note how the diameter of the groove has been set to be the same as the diameter of the case, resulting in a rectangular groove profile, rather than the trapezoid that is more frequently used.

Defect Search

Once the case regions have been defined, a buffer distance is applied to the inside edges of each region. These buffered regions define the area within which the defect searches will be conducted. By buffering the inspection regions, edge anomalies and non-ideal lighting frequently found near the boundaries are ignored. The size of the buffers can be independently adjusted for each region as part of the standard user interface and is saved in the part profile. This concept is demonstrated in FIG. 13.

There are two general defect detection algorithms that can be conducted in each region. These two algorithms are closely tied to the detection of dents and perforations respectively as discussed above in the lighting section. More generally however, they correspond to the recognition of a group of dark pixels on a bright background or a group of bright pixels on a dark background.

Although there are only two defect detection algorithms used across all the regions on the part, the parameters associated with the algorithm can be modified from region to region. Additionally, the detection of dark and/or bright defects can be disabled for specific regions. This information is saved in the part profile.

Dark Defects

The detection of dark defects is a 6 step process.

1. Logarithm: Each, pixel brightness value (0-255) is replaced with the log of its brightness value. This serves to expand the brightness values of darker regions while compressing the values of brighter regions, thereby making it easier to find dark defects on a dim background.

2. Sobel Magnitude Operator: The Sobel Operator is the derivative of the image. Therefore, the Sobel Magnitude is shown below:

$$S_M = \sqrt{\left(\frac{\partial f}{\partial x}\right)^2 + \left(\frac{\partial f}{\partial x}\right)^2}$$

although it is frequently approximated as the following:

$$S_M = \frac{\frac{\partial f}{\partial x} + \frac{\partial f}{\partial y}}{2}$$

The Sobel Magnitude Operator highlights pixels according to the difference between their brightness and the brightness of their neighbors. Since this operator is performed after the Logarithm filter applied in step 1, the resulting image will emphasize dark pockets on an otherwise dim background. After the Sobel Magnitude Operator is applied, the image will contain a number of bright 'rings' around the identified dark defects.

3. Invert Original Image: The original image captured by the camera is inverted so that bright pixels appear dark and dark pixels appear bright. This results in an image with dark defect areas appearing as bright spots.

4. Multiplication: the image obtained after step 2 is multiplied with the image obtained after step 3. Multiplication of two images like this is functionally equivalent to performing an AND operation on them. Only pixels which appear bright in the resultant image. In this case, the multiplication of these two images will result in the highlighting of the rings found in step two, but only if these rings surround a dark spot.

5. Threshold: All pixels with a brightness below a specified value are set to OFF while all pixels greater than or equal to the specified value are set to ON.

6. Fill in Holes: The image obtained after the completion of steps 1-5 appears as a series of ON-pixel rings. The final step is to fill in all enclosed contours with ONpixels.

After completing these steps, the resultant image should consist of a pixels corresponding to potential defects. These bright blobs are superimposed on areas that originally contained dark defects.

The detection of bright defects is a two-step process.

1. Threshold: Apixel brightness threshold filter may be applied to pick out all saturated pixels (greyscale 255). A user-definable threshold may be provided so values lower than 255 can be detected.

2. Count Filter: A count filter is a technique for filtering small pixel noise. A size parameter is set (2, 3, 4, etc) and a square box is constructed whose sides are this number of pixels in length. Therefore, if the size parameter is set to 3, the box will be 3 pixels by 3 pixels. This box is then centered on every pixel picked out by the threshold filter applied in step 1. The filter then counts the number of additional pixels contained within the box which have been flagged by the threshold filter and verifies that there is at least one other saturated pixel present. Any pixel which fails this test has its brightness set to 0. The effect of this filter operation is to blank out isolated noise pixels.

Once these two steps have been completed, the resultant binary image will consist of ON pixels corresponding to potential defects. Furthermore, any "speckling" type noise in the original image which would have results in an ON pixel will have been eliminated leaving only those pixels which are in close proximity to other pixels which are ON.

Pixel Count

After bright and/or dark defect detection algorithms have been run in a given region, the resultant processed images are binary. These two images are then OR'ed together. This results in a single image with both bright and dark defects.

The software now counts the number of ON pixels in each detected defect. Finally, the part will be flagged as defective if either the quantity of defect pixels within a given connected region is above a user-defined threshold, or if the total quantity of defect pixels across the entire part is above a user-defined threshold.

Thread Signal/Data Processing

Introduction

What follows is a description of a thread parameter estimation process. This process which is described in general in published U.S. patent application 2010/0238435 provides one embodiment of a standard thread measurement "feature" in the method and system of the invention.

Thread Signal Processing

Thread signal processing is the process of estimating the following thread parameters.

1) pitch
2) major diameter
3) minor diameter
4) functional diameter
5) lead deviation
6) pitch diameter As the thread signal processing proceeds, a number of intermediate data products are produced in early processing stages that are further analyzed in later stages. These include:

roughpos/neg crossinglocations
roughcrest locations
wire position search intervals
left/right flank lines
wire positions
precise crest/root locations
3-crest average/median measurements of major diameter, minor diameter, pitch diameter
3-D crest cylinder axis
wire position projections on the 3-D crest cylinder axis
3-D crest cylinder diameter
3-D crest root-mean-square distance between crest data and fit.

These intermediate data products are analyzed to produce final estimates of the thread parameters. For example major diameter is estimated as twice the radius of the 3-D crest cylinder. The 3-D crest cylinder axis then depends on the precise crest/root locations. The crest/root locations then depend on the search intervals based on rough crest locations and pos/neg crossings, and on data from the original calibrated part data.

Processing Restrictions

Inspection Region

The thread processing occurs between position limits called an inspection region. In template editor, the user specifies the inspection region by manipulating the upper and lower stage position limits, overlaid on an image of the part.

These limits utilize the calibrated sensor position so that measurements by are aligned to the approximately similar physical positions on the part.

The estimation of thread parameters is specified to be an average estimate over all the data within which the inspection region. In practice, some of the intermediate data products are estimated outside of the inspection region in order to allow estimation of all thread parameters within the full region. For example, a wire position within the inspection region may require a thread crest outside the inspection region.

Measurement Assumption for the Inspection Region

The following requirements guide the user's placement of the inspection region on the image of the part.

The first assumption is that the thread parameters be constant throughout the inspection region. This enables the software to average the estimates from different positions within the inspection region and not be concerned with partitioning or segmenting the data into different regions for special processing.

This requirement excludes the following types of data from the inspection region:

the beginning or end of a threaded region, with thread crests less than full height.

a threaded region with a taper.

a threaded region with a notch or extensive damage.

A second assumption is that the inspection region contains at least 4-6 thread pitches. This amount of data is required to construct several of the intermediate data products with the required accuracy.

A third assumption is that the thread be manufactured with a 60-degree flank angle. Thread processing implicitly utilizes this parameter in several places. One of the most direct usages is the conversion of lead deviation into functional diameter.

A fourth assumption is that the thread has a cylindrical cross section. Non-cylindrical threads would require the 3-D peak cylinder to be suitably generalized. Incorrect fit to a non-cylindrical cross section would lead to incorrect lead deviation measures.

A fifth assumption is that the thread has a single helix.

Measurement of the following threaded fasteners are provided:

non-standard thread types, especially self-tapping screws, small threaded regions with 2 or 3 pitches.

Taptite trilobe threaded regions.

Rough Crossings

The thread model describes herein below is a sampled representation of one thread profile, for exactly one pitch. Thread model starts at the midpoint of a rising thread flank and ends one pitch later.

Using a correlation detector the thread model is matched to data within the inspection regions producing thresholded detections within the inspection region, that are called crossings.

"Refinements" noted hereinmay make the crossings more accurate. The refinements also separate the crossings into positive crossings and negative crossings. The thread model is a lateral sequence of points that represent a best estimate of the outline of one cycle of the thread form.

Rough Crest and Root Positions

A crest/root detector extracts rough crest and root positions between the matched adjacent pairs of positive and negative crossings.

Pitch Estimate

A pitch estimate is required for step set gage wire diameter. The estimate is required to be accurate enough to unambiguously select a unique gage wire from the set appropriate for the measurement. The current process utilizes a two-stage process.

This process may be simplified as described herein.

First Estimate.

Crossing data is analyzed and averaged over all sensors to create a thread pitch estimate, the "crossing pitch."

Second Pitch Estimate

The steps set wire gage diameter, wire position search intervals, measure flank lines and measure 3-point diameters noted herein below are completed in a first iteration. Then the wire positions are averaged over all sensors and positions to compute a pitch estimate.

Set Gage Wire Diameter

Gage wires are utilized in physical thread measurements of pitch diameter in the prior art. Two wires are placed in adjacent threads on one side of the part, and a single wire is placed on the other side of the part. A micrometer measures the distance between the reference line established by the two adjacent gage wires and the reference point established by the other gage wire. A tabulated correction formula converts the micrometer distance to an estimate of the pitch diameter.

Gage wire sizes are thus selected prior to the thread measurement. To do this one estimates the thread pitch as previously described and then one selects the closest gage wire in a set to the pitch estimate. The gage wire set utilized is the one appropriate to the type of measurement; currently there is one set for the metric coarse thread sequence, and another for a similar English thread set. The gage wire sets are chosen at part template edit time by making a selection in a pull down list.

Wire Position Search Intervals

One places "virtual" gage wires onto the calibrated sensor data throughout the inspection region. In order to place the "virtual" gage wires we must identify search intervals for each wire to be located.

A requirement of the following processing steps is that the wire positions in the inspection region have no gaps. Another requirement is that a wire position search interval consist of two valid thread crests, one valid thread root between the two thread crests, and valid positive/negative crossings between the crest/root pairs.

One then searches the set of positive/negative crossings and crest/root positions for the set of wire position search intervals to analyze. The result of intervals, one set per sensor.

Measure Flank Lines

For a left flank all data is analyzed between the rough positions of the left crest and the central root. One then determines the height limits of a flank line data extraction region that covers 70% (a configurable parameter) of the height interval between left crest and central root. This data is extracted into a data set and fit to a line, becoming the left flank line.

The procedure avoids the non-linear regions near the left crest and central root. In addition, a "flank line valid" flag is computed, based on the RMS distance between the left flank line and the data within the left flank line data extraction region. If the RMS distance between the flank line and the data points in the flank line data extraction interval is larger than 10 pm per point (a configurable parameter), then the flag is set to invalid.

The process is repeated for the right flank line and then for all wire position search intervals.

Measure Wire Positions

The wire positions are calculated, given the left and right flank lines and the wire size. The virtual wire is tangent to each flank line and the resulting position is calculated with a simple geometric formula.

The position has a valid flag that is true when both flank lines are valid, and false otherwise.

Measure 3-Point Diameters

The 3-point technique is a method to measure the minor, major, and pitch diameters without explicitly utilizing 3-D information.

For example, consider the major diameter. It is defined as the diameter of a cylinder that contains all the inspection region's thread crests.

In this method, the top of a thread crest in calibrated sensor coordinates forms an elementary measurement. The elementary measurements are combined into triplets for further analysis. Only crests from the two sensors of a single laser are combined.

Two adjacent thread crest positions are combined with the thread crest position that is closest to the average position of crests. The two crests form a reference line. Then the distance from the reference line to the crest is computed. This is the 3 crest distance for that crest triplet.

In this manner, the 3-crest distances from all adjacent crest triplets are computed. The 3-crest distances are all added to a data vector. The 3-crest diameter measurement is either the average or the median of all the 3-crest distances within the 3-crest data vector.

3-Point Minor Diameter

The 3-point minor diameter computes 3-point distances using precise root locations in the sensor data. The 3-point minor diameter is the average of the 3-point distance vector.

3-Point Major Diameter

The 3-point major diameter computes 3-crest distances using precise crest locations in the sensor data. The 3-point major diameter is the median of the 3-point distance vector.

3-Point Wire Pitch Diameter

The 3-point pitch diameter computes 3-point distances using the wire positions computed in the sensor data. The 3-point wire pitch diameter is the median of the 3-pointwire pitch diameter.

Figure 14:
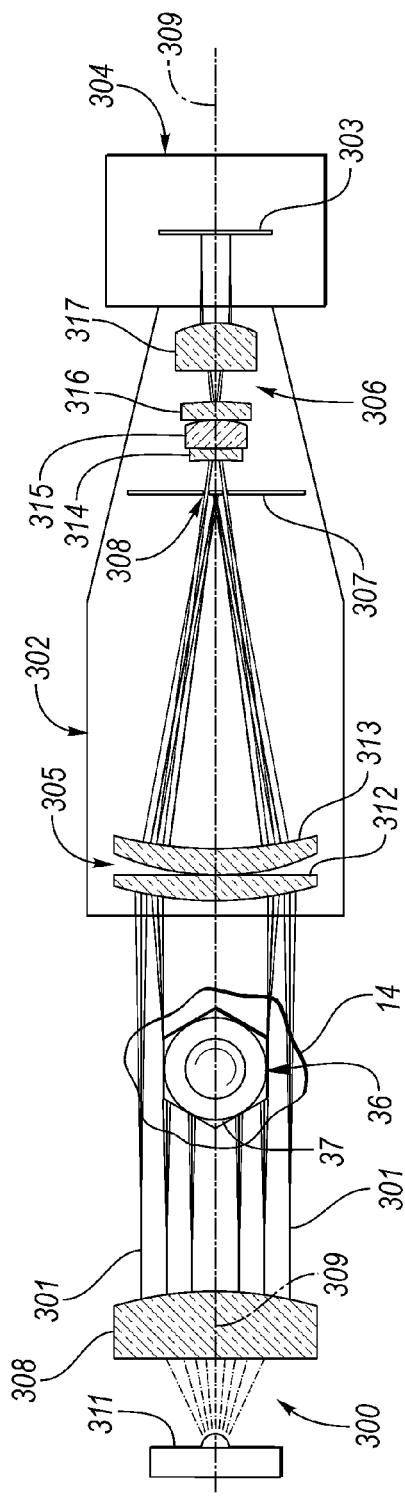
FIG. 14 is a top plan schematic view, partially broken away and in cross section, of an illumination assembly and a telecentric lens and detector assembly of FIGS. 3, 12 and 13 with a threaded fastener at the inspection station with some radiation blocked by the threaded fastener and some radiation scattered by the edges of the threaded fastener and through a diaphragm of the telecentric lens.

FIG. 14 is screen shot from a user interface of a PC which illustrate intermediate data extracted from a M16×1.5 thread plug gage.

Measure 3-D Crest Cylinder

The measured thread crest position data is analyzed to obtain a 3-D cylinder with least squares methods. The 3-D crest cylinder fit has several output parameters of interest.

the RMS distance between the crest position data and the fitted shape.

the 3-D location of the cylinder's central axis.

the radius of the cylinder

Project Wire Positions onto 3-D Crest Cylinder Axis

Measured wire positions can be combined with the 3-D location of the 3-D crest cylinder's central axis. An imaginary disk, perpendicular to the cylinder axis that goes through the measured wire position marks a position on the 3-D crest cylinder axis.

A data set consisting of the projections of all sensor wire positions is constructed.

The output intermediate data is a vector, sorted from minimum to maximum sensor stage position of the projected wire positions.

Thread Parameter Estimation

Thread parameter estimation utilizes the intermediate data products and may also correct them based on a model of the measurement, prior to producing a final thread parameter estimate.

Wire Pitch

Thread pitch is estimated from the wire center intermediate data. For each sensor data set the adjacent pairs of wire positions are used to calculate an adjacent wire pitch, one per adjacent wire positions. For all lasers, each wire pitch is added to a wire pitch vector.

The wire pitch estimate is the median of the elements in the wire pitch vector.

Major Diameter

Thread major diameter is typically reported as the diameter of the 3-D crest cylinder.

If the 3-D crest cylinder fit was unsuccessful, the major diameter is estimated in a different way, detailed below. The cylinder fit can fail due to several factors listed here:

part inclined at too great an angle with respect to the stage axis.

thread crest positions do not fit a cylinder, the RMS fit-to-data distance is too large.

When the cylinder fit fails the major diameter is estimated from the 3-point major diameter data. This case is special because a previous condition (cylinder fit) has already failed. In practice, the cylinder fit most often failed when the threaded region was too short or the inspection extended beyond the end of the threaded region.

Because of this bias a simple median of the 3-point major diameter data would typically be too low, most of the good 3-point data was concentrated at the highest measurements. In this case the major diameter estimate is the value such that 20% of the 3-point data is higher and 80% of the 3-point data is lower.

Calibration Correction

Major diameter is also corrected by a final end-to end calibration of the total system. The reported major diameter is often two low, with bias ranging from −20 μm to 0.

After diameter calibration the system is exposed to a set of measured thread plug gages. One then plots their major diameter bias as a function of diameter and fit a simple segmented line to the bias results. These bias fits then are entered into the system configuration file and are used to correct the measured major diameter with the measured bias.

Minor Diameter

Thread minor diameter is estimated with the 3-point minor diameter distance vector. The minor diameter value is the average of the elements in the distance vector.

Pitch Diameter

Pitch diameter estimation uses two sets of intermediate data products, the wire positions and the 3-D crest cylinder fit.

The pitch diameter estimate calculation is presented in a step-by-step list below:

a) Compute the pitch diameter contact points with the thread flanks by calculating the intersection of the wire shape with the left or right flank lines.

b) Average the left and right points of intersection, and compute the distance (radius) from the average point to the 3-D crest cylinder fit axis. This is the pitch diameter radius for each wire position.

c) Calculate the average value of the pitch diameter radius.

d) Correct each average wire position radius for the part projection angle, using the angle of the 3-D crest cylinder axis to the stage axis, projected into the sensor's coordinate system.

e) Add left and right sensor corrected pitch diameter radius estimates to product an estimate of the pitch diameter for each view.

f) Average the laser estimates to produce the system pitch diameter estimate.

Correction for Part Projection Angle

The computation of pitch diameter is complicated by projection effects. The light performs an almost perfect orthographic (shadow) projection of the thread's shape. However, the projection is not the same thing as the thread cross section, which is specified in thread design documents. The cross section is the thread shape if it were cut by a plane going through the thread's central axis.

The difference is caused by the thread lead angle, which is in the range of 1-3 degrees for many typical threads. The lead angle means that the thread cross section is most accurately viewed in shadow when the viewing direction coincides with the direction of the lead.

It is impossible to position the thread so that a shadow view of the thread is simultaneously aligned with the top and bottom threads. For the example of a thread with a 3 degree lead angle, tilting the thread to align the top of the thread with the viewing angle will make the angle between the lead and the viewing angle for the bottom thread about 6 degrees.

A correction factor was developed for this effect. If one knows to tilt of the thread with respect to the viewing angle then you can correct the observed pitch diameter radius for the expected bias caused by the projection angle. This correction is precomputed and stored in a table.

For each view the tilt of the thread with respect to the viewing angle can be obtained from the 3-D cylinder fit axis. Separate corrections are applied for the different views.

Calibration Correction

Pitch diameter is also corrected by a final end-to-end calibration of the total system. The reported pitch diameter is often too high, with bias ranging from +5 μm to +35 μm.

After diameter calibration, one exposes the system to a set of measured thread plugs gages. One then plots their pitch diameter bias as a function of diameter and fit a simple segmented line to the bias results. These bias fits then are entered into the system calibration file and are used to correct the measured pitch diameter with the measured bias.

Lead Deviation

The lead deviation estimate uses the wire pitch and the locations of the wire positions as projected onto the 3-D cylinder fit axis.

For an ideal helical thread, the wire position projections should result in a regular pattern along the 3-D cylinder fit axis. Lead deviation is the deviation of that pattern from the ideal, measured as a maximum distance of any projected wire position from the ideal pattern.

The computation of the lead deviation estimate follows a step-by-step procedure:

a) Create a wire position projection vector, containing all the data.

b) Sort the wire position projection vector in order of position along the 3-D cylinder fit axis.

c) Convert the wire positions of the elements of the vector into degrees, by multiplying by the factor (360/pitch) and then reducing the element values modulo 360.

d) Calculate an offset value so that the maximum absolute value of the degree-valued element positions is minimal. For example with a lead deviation of 0.010 mm for a 1 mm pitch thread, the absolute value of at least one degree value element position would be 3.60 degrees (0.010) mm/1 mm equals (1/100) and 360/100 is 3.60)

Convert the value from degrees to mm and report as the lead deviation estimate.

All lead deviation estimates are positive.

Calibration Correction

Errors in measurement mean that the physical measurement of a perfect thread will have a positive lead deviation.

To attempt to correct for this effect, one measures the lead deviation for a set of thread plug gages and plotted them as a function of gage diameter. The most common form observed is a constant lead deviation of 0.010 mm to 0.20 mill.

This value observed in calibration with thread gages is taken to be a bias. This amount of bias is entered into the system calibration file and used to correct the measured lead deviation for this measurement bias.

Functional Diameter

Functional diameter is currently defined in practice by the fit of a special fit gage over the thread. The special fit gage is essentially a nut that is split in two by a plane cut through the central axis of the nut. The two halves of the fit gage are held in a fixture that measures the distance between the two halves. There is one special fit gage for every thread type.

Functional diameter is defined as the pitch diameter when the special fit gage is clamped tightly over a thread plug setting gage. When one puts a different part into the fit gage the fit gage may expand slightly, due to a summation of effects involving the differences between the part and the thread plug setting gage used to setup the functional diameter measurement. The functional diameter measurement is then the thread plug setting gage's pitch diameter plus the additional separation between the two fit gage pieces.

Functional Diameter Estimator

The functional diameter measurement method is an approximation of the fit gage method. We do not perform a full 3-D analog of the physical fit gage. Instead we have made an approximation that involves the use of lead deviation and the shape of the thread form If we imagine the thread form as perfect and also having a 60 degree flank angle then lead deviations should cause the thread form fit gage pieces to move apart. A single lead deviation either up or down the thread form axis will cause a single split piece of the fitting gage to move outward. The amount of outward movement for a 60 degree flank angle will be equal to (V) (lead deviation). The movement provides a clearance for both positive and negative movements of the lead, relative to a perfect helical shape.

$$FD = PD + \sqrt{3}(\text{Lead Deviation})$$

Learning the Thread Model

The thread model is a learned sequence of points that represent a best estimate of the outline of one cycle of the thread form. The thread model is calculated when the inspection region is specified, at template edit time.

The measure template routine uses a pattern match algorithm with a sine wave pattern to identify periodically in the inspection region data. This process determines an approximate thread pitch. The process also calculates a starting point in the data vector for the first beginning of the matched pattern, which is an approximation to the first midpoint of a right flank line.

With the pitch and the starting point in hand, the measure template routine can then calculate an average thread model. Starting with the first sample point in the matched pattern, points that are 1, 2, 3, . . . , N pitches later in the inspection region are averaged to form the first point of the thread model. The process is repeated for all the rest of the points in the first matched pattern. The thread model is then stored in the template for later use.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of inspecting a manufactured part at an inspection station having a measurement axis, the method comprising the steps of:

supporting a part having opposite ends, a length between the ends, a width and a part axis wherein the part has backside and frontside surfaces when supported;

rotating the supported part about the measurement axis so that the part moves at predetermined angular increments during at least one rotational scan;

directing a backside beam of collimated radiation at substantially the entire backside surface of the supported part at each of a first plurality of consecutive angular increments of movement, wherein the backside beam is occluded by the supported part at each of the first plurality of consecutive increments of movement to create a stream of unobstructed portions of the backside beam in rapid succession passing by and not blocked by the supported part;

directing a frontside beam of radiation at at least a portion of the entire frontside surface of the supported part at each of a second plurality of consecutive angular increments of movement, wherein the frontside beam is reflected by the supported part at each of the second plurality of consecutive increments of movement to create a stream of reflected portions of the frontside beam in rapid succession;

detecting the streams of reflected and unobstructed portions at the inspection station to obtain electrical signals; and processing the electrical signals to determine at least one geometric dimension and any visual defects of the part.

2. The method as claimed in claim 1, wherein substantially the entire backside surface is completely enclosed by a beam profile of the backside beam.

3. The method as claimed in claim 2, wherein the beam profile is rectangular with a height greater than or equal to the length of the part and a width greater than or equal to the width of the part.

4. The method as claimed in claim 1, wherein the streams of reflected and unobstructed portions are detected at a single image plane.

5. The method as claimed in claim 1, further comprising centering and aligning the part axis with the measurement axis.

6. The method as claimed in claim 1, further comprising projecting focused lines of radiation at the frontside surface of the supported part during the at least one rotational scan to obtain reflected radiation and sensing the reflected radiation to obtain electrical signals.

7. The method as claimed in claim 6, wherein the focused lines of radiation at the frontside surface are strobed.

8. The method as claimed in claim 1, wherein the first and second plurality of consecutive angular increments are coincident.

9. A system for inspecting a manufactured part at an inspection station having a measurement axis, the system comprising:

a fixture to support a part having opposite ends, a length between the ends, a width and a part axis, wherein the part has backside and frontside surfaces when supported;

a motor to rotatably drive the fixture about the measurement axis at predetermined angular increments of movement during at least one rotational scan;

a back light to direct a backside beam of collimated radiation at substantially the entire backside surface of the supported part at each of a first plurality of consecutive angular increments of movement wherein the backside beam is occluded by the supported part at each of the first plurality of consecutive increments of movement to create a stream of unobstructed portions of the backside beam in rapid succession passing by and not blocked by the supported part;

a front light to direct a frontside beam of radiation at at least a portion of the entire frontside surface of the supported part at each of a second plurality of consecutive angular increments of movement wherein the frontside beam is reflected by the supported part at each of the second plurality of consecutive angular increments of movement to create a stream of reflected portions of the frontside beam in rapid succession;

a lens and detector assembly to image and detect the streams of reflected and unobstructed portions at the inspection station to obtain electrical signals; and at least one processor to process the electrical signals to determine at least one geometric dimension and any visual defects of the part.

10. The system as claimed in claim 9, wherein substantially the entire backside surface is completely enclosed by a beam profile of the backside beam.

11. The system as claimed in claim 10, wherein the beam profile is rectangular with a height greater than or equal to the length of the part and a width greater than or equal to the width of the part.

12. The system as claimed in claim 9, wherein the streams of reflected and unobstructed portions are detected at a single image plane of the lens and detector assembly.

13. The system as claimed in claim 9, further comprising a part centering and aligning subsystem to center and align the part axis with the measurement axis.

14. The system as claimed in claim 9, further comprising a triangulation-based sensor configured to project focused lines of radiation at the frontside surface of the supported part during the at least one rotational scan and to sense corresponding reflected lines of radiation to obtain electrical signals.

15. The system as claimed in claim 14, wherein the focused lines of radiation are strobed.

16. The system as claimed in claim 9, wherein the front light includes an array of spaced light sources.

17. The system as claimed in claim 16, wherein each of the light sources is a light emitting diode.

18. The system as claimed in claim 16, wherein the light sources are arranged in a curved arrangement.

19. The system as claimed in claim 9, wherein the motor is a stepper motor.

* * * * *